(12) United States Patent
Wu et al.

(10) Patent No.: US 12,016,925 B2
(45) Date of Patent: Jun. 25, 2024

(54) CARBOHYDRATE COMPOSITION AS PHARMACEUTICAL INGREDIENT AND USE THEREOF

(71) Applicants: Medgaea Japan Co., Ltd., Tokyo (JP); Medgaea Life Sciences Ltd., New Taipei (TW)

(72) Inventors: Chang-Jer Wu, Taipei (TW); Bo-Rui Chen, Taichung (TW); Chih-Chun Hong, Tokyo (JP); Yuh-Ting Huang, Tokyo (JP); Masahiko Iha, Okinawa (JP); Makoto Tomori, Okinawa (JP)

(73) Assignees: Medgaea Japan Co., Ltd., Tokyo (JP); Medgaea Life Sciences Ltd., New Taipei (TW)

( * ) Notice: Subject to any disclaimer, the term of this patent is extended or adjusted under 35 U.S.C. 154(b) by 0 days.

(21) Appl. No.: 17/666,529

(22) Filed: Feb. 7, 2022

(65) Prior Publication Data
US 2022/0249671 A1    Aug. 11, 2022

Related U.S. Application Data

(60) Provisional application No. 63/147,205, filed on Feb. 8, 2021.

(51) Int. Cl.
| | |
|---|---|
| *A61K 47/26* | (2006.01) |
| *A61K 31/573* | (2006.01) |
| *A61K 31/7004* | (2006.01) |
| *A61K 31/7012* | (2006.01) |
| *A61P 17/00* | (2006.01) |

(52) U.S. Cl.
CPC ............ *A61K 47/26* (2013.01); *A61K 31/573* (2013.01); *A61K 31/7004* (2013.01); *A61K 31/7012* (2013.01); *A61P 17/00* (2018.01)

(58) Field of Classification Search
CPC ...... C08B 37/00; A61K 47/26; A61K 31/573; A61K 31/7004; A61K 31/7012; A61P 17/00
USPC .......................................................... 514/23
See application file for complete search history.

(56) References Cited

U.S. PATENT DOCUMENTS

2005/0130934 A1* 6/2005 Nagaoka .................... A61P 1/04
536/54

FOREIGN PATENT DOCUMENTS

| CN | 104173867 | 12/2014 |
|---|---|---|
| CN | 105030562 | 11/2015 |
| CN | 110785161 | 2/2020 |
| WO | 2016085366 | 6/2016 |

OTHER PUBLICATIONS

Lim et al ("Structural elucidation of fucoidan form Cladosiphon Okamuranus (Okinawa.mozuku)", Food Chemistry 272 (2019) 222-226) (Year: 2019).*
Tomori et al ("Evaluation of the Immunomodulatory Effects of Fucoidan Derived from Cladosiphon Okamuranus Tokida in Mice", Marine Drugs, 17, 547, 2019) (Year: 2019).*
Chen et al. Immunomodulation and mechanisms of fucoidan from Cladosiphon okamuranus ameliorates atopic dermatitis symptoms. International Journal of Biological Macromolecules 189 (2021) 537-543 (Available online Aug. 18, 2021) (Year: 2021).*
Chen et al. Topical application of fucoidan derived from Cladosiphon okamuranus alleviates atopic dermatitis symptoms through immunomodulation. International Immunopharmacology 101 (2021) 108362, pp. 1-9. (Available online Nov. 18, 2021) (Year: 2021).*
Hasegawa, et al., "Suppression of Allergic Contact Dermatitis by a-L-fucose", The Journal of Investigative Dermatology, 1980, pp. 284-287.
Wang et al., "Research progress on biological activity of fucoidan from Phaeophyta", Journal of Zhejiang University of Technology, with English abstract, Apr. 2018, pp. 209-215.
"Office Action of Taiwan Counterpart Application", issued on Jul. 27, 2022, p. 1-p. 8
Hong Wang et al., "Research progress on biological activity of fucoidan from Phaeophyta", with English abstract thereof, Journal of Zhejiang University of Technology, Apr. 2018, pp. 209-215.
Ying Liu et al., "Advances on Fucoidan", with English abstract thereof, Food and Fermentation Industries, Dec. 2011, pp. 146-155, No English Language translation provided.
Junxin Wang et al., "Hypolipidemic effect and related gene expression of fucoidan from kelp Laminaria japonica", with English abstract thereof, Journal of Dalian Ocean University, Jun. 2020, pp. 339-346.
Solabia Group, "Application of Fucoidan (FUCOGEL-1000) in the Cosmetics Industry", with English abstract thereof, China Cosmetics, Dec. 2002, pp. 1-4.
Bo-Rui Chen et al., "Immunomodulation and mechanisms of fucoidan from Cladosiphon okamuranus ameliorates atopic dermatitis symptoms", International Journal of Biological Macromolecules, Oct. 2021, pp. 537-543.
Bo-Rui Chen et al., "Topical application of fucoidan derived from Cladosiphon okamuranus alleviates atopic dermatitis symptoms through immunomodulation", International Immunopharmacology, Dec. 2021, pp. 1-9.

* cited by examiner (Continued)

*Primary Examiner* — Yih-Horng Shiao
(74) *Attorney, Agent, or Firm* — JCIPRNET

(57) ABSTRACT

A carbohydrate composition includes fucose, glucuronic acid, galactose, and arabinose. Based on the total weight of the carbohydrate composition, the content of fucose is 45.5% to 76% by weight; the content of glucuronic acid is 11% to 19% by weight; the content of galactose is 4.5% to 14.5% by weight, and the content of arabinose is 5.5% to 18% by weight. A pharmaceutical ingredient including the above-mentioned carbohydrate composition is provided.

11 Claims, 25 Drawing Sheets

CARBOHYDRATE COMPOSITION AS PHARMACEUTICAL INGREDIENT AND USE THEREOF

CROSS-REFERENCE TO RELATED APPLICATION

This application claims the priority benefit of U.S. application Ser. No. 63/147,205, filed on Feb. 8, 2021. The entirety of the above-mentioned patent application is hereby incorporated by reference herein and made a part of this specification.

BACKGROUND

Technical Field

The disclosure relates to a carbohydrate composition as a pharmaceutical ingredient, and more particularly, to a pharmaceutical ingredient of a carbohydrate composition that may nourish skin, inhibit skin allergies, inhibit skin inflammation, or improve atopic dermatitis.

Description of Related Art

Atopic dermatitis (AD), also referred to as atopic eczema, is an allergic skin disease. The typical symptoms of atopic dermatitis are dry skin accompanied by skin allergies or skin inflammation such as severe itching, and swollen skin from scratching. However, long-term scratching may cause lack of sleep and poor spirits of patients, which may lead to inability to concentrate and affect the quality of life, and may even worsen the symptoms and increase the risk of bacterial skin infections.

The current drugs for treating atopic dermatitis include steroids, antihistamines, immunosuppressants, etc., and are mainly based on steroids. However, although steroids may control the condition of dermatitis, long-term use may cause side effects such as skin atrophy, vasodilatation, affect the secretion of adrenaline, and affect growth.

SUMMARY

The disclosure provides a carbohydrate composition and a pharmaceutical ingredient, which may have effects of nourishing skin, inhibiting skin allergies, inhibiting skin inflammation, or improving atopic dermatitis.

The carbohydrate composition in the disclosure includes fucose, glucuronic acid, galactose, and arabinose. Based on a total weight of the carbohydrate composition, a content of fucose is 45.5% to 76% by weight; a content of glucuronic acid is 11% to 19% by weight; a content of galactose is 4.5% to 14.5% by weight, and a content of arabinose is 5.5% to 18% by weight.

In an embodiment of the disclosure, based on the total weight of the carbohydrate composition, the content of fucose is 49.5% to 72.5% by weight; the content of glucuronic acid is 11% to 17.5% by weight; the content of galactose is 6% to 14% by weight, and the content of arabinose is 8.5% to 16% by weight.

In an embodiment of the disclosure, based on the total weight of the carbohydrate composition, the content of fucose is 52% to 69% by weight; the content of glucuronic acid is 11.5% to 17% by weight; the content of galactose is 6.5% to 13.5% by weight, and the content of arabinose is 9% to 15.5% by weight.

In an embodiment of the disclosure, the carbohydrate composition is an oral preparation.

In an embodiment of the disclosure, a dose range of the carbohydrate composition in the oral preparation ranges from 50 mg/kg to 800 mg/kg.

In an embodiment of the disclosure, the carbohydrate composition is a topical preparation.

In an embodiment of the disclosure, a dose range of the carbohydrate composition in the topical preparation ranges from 35 mg/mL to 70 mg/mL.

In an embodiment of the disclosure, the carbohydrate composition is the topical preparation and the oral preparation.

In an embodiment of the disclosure, the dose range of the carbohydrate composition in the topical preparation ranges from 35 mg/mL to 70 mg/mL, and the dose range of the carbohydrate composition in the oral preparation ranges from 50 mg/kg to 800 mg/kg.

A use of the carbohydrate composition in the disclosure may be used to prepare a drug for inhibiting the skin allergies, inhibiting the skin inflammation, or improving atopic dermatitis.

The use of the carbohydrate composition in the disclosure may be used to prepare health food or a care product for nourishing the skin.

A pharmaceutical ingredient in the disclosure includes the carbohydrate composition and an additive.

Based on the above, in the carbohydrate composition and the pharmaceutical ingredient in the embodiments of the disclosure, the carbohydrate composition may include fucose of 45.5% to 76% by weight, glucuronic acid of 11% to 19% by weight, galactose of 4.5% to 14.5% by weight, and arabinose of 5.5% to 18% by weight. Therefore, the carbohydrate composition and the pharmaceutical ingredient containing the carbohydrate composition have the effects of nourishing the skin, inhibiting the skin allergies, inhibiting the skin inflammation, or improving atopic dermatitis, and having no side effects.

In order for the aforementioned features and advantages of the disclosure to be more comprehensible, embodiments accompanied with drawings are described in detail below.

DETAILED DESCRIPTION OF DISCLOSED EMBODIMENTS

Figure 1A:
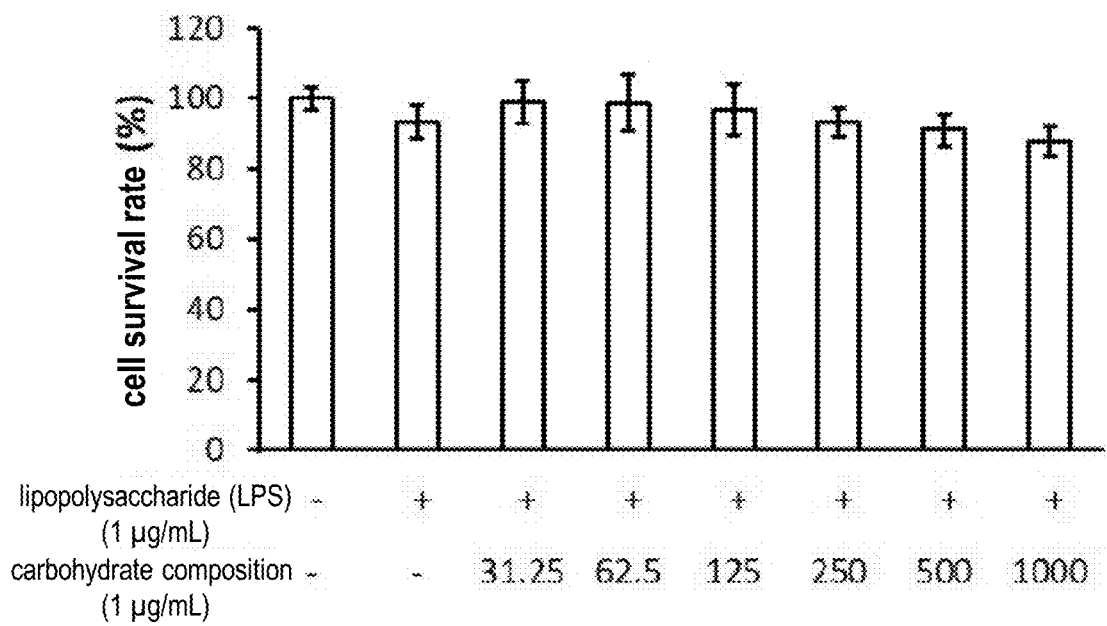
FIGS. 1A to 1B show an effect on cytotoxicity of a carbohydrate composition in this embodiment to RAW264.7 macrophages and production of nitric oxide.

A carbohydrate composition in this embodiment may substantially formed by fucose, glucuronic acid, galactose, arabinose, and other carbohydrates. The other carbohydrates may include glucose, but the disclosure is not limited thereto.

In this embodiment, based on a total weight of the carbohydrate composition, a content of fucose may be, for example, 45.5% to 76% by weight. A content of glucuronic acid may be, for example, 11% to 19% by weight. A content of galactose may be, for example, 4.5% to 14.5% by weight. A content of arabinose may be, for example, 5.5% to 18% by weight, and a content of the other carbohydrates may be, for example, 0% to 3.5% by weight. However, the disclosure is not limited thereto.

In some embodiments, in order to better improve atopic dermatitis, based on the total weight of the carbohydrate composition, the content of fucose may be, for example, 49.5% to 72.5% by weight. The content of glucuronic acid may be, for example, 11% to 17.5% by weight. The content of galactose may be, for example, 6% to 14% by weight. The content of arabinose may be, for example, 8.5% to 16% by weight, and the content of the other carbohydrates may be, for example, 0% to 3.5% by weight. However, the disclosure is not limited thereto.

In some embodiments, in order to better improve atopic dermatitis, based on the total weight of the carbohydrate composition, the content of fucose may be, for example, 52% to 69% by weight. The content of glucuronic acid may be, for example, 11.5% to 17% by weight. The content of galactose may be, for example, 6.5% to 13.5% by weight. The content of arabinose may be, for example, 9% to 15.5% by weight, and the content of the other carbohydrates may be, for example, 0% to 3.5% by weight. However, the disclosure is not limited thereto.

In this embodiment, the carbohydrate composition may be, for example, derived from a natural algae extract or a carbohydrate mixture. Based on the total weight of the carbohydrate composition, a content of the carbohydrate composition may be, for example, greater than 95% by weight. However, the disclosure is not limited thereto. In this embodiment, the natural algae extract may be, for example, a brown algae extract. For example, the natural algae extract may be, for example, a cladosiphon okamuranus (or okinawa mozuku) extract. However, the disclosure is not limited thereto.

In this embodiment, the carbohydrate composition may be used as a topical preparation. The topical preparation may be, for example, liquor, dust, granules, sprays, ointment, cream, latex, gel, or patch. However, the disclosure is not limited thereto. In this embodiment, an effective dose range of the carbohydrate composition in the topical preparation may range, for example, from 35 mg/mL to 70 mg/mL. However, the disclosure is not limited thereto. In this embodiment, based on a total weight of the topical preparation, the content of the carbohydrate composition may be, for example, 70% by weight, and a content of an additive may be, for example, 30% by weight. However, the disclosure is not limited thereto. In this embodiment, the additive in the topical preparation may include olive oil and emulsifiers. However, the disclosure is not limited thereto.

In this embodiment, the carbohydrate composition may also be an oral preparation. The oral preparation refers to administration in an oral form, or may be suitable for oral administration. The oral preparation may be, for example, capsules, tablets, pills, granules, powders, drops, and dripping pills. However, the disclosure is not limited thereto. In this embodiment, the effective dose range of the carbohydrate composition in the oral preparation may range, for example, from 50 mg/kg to 800 mg/kg. However, the disclosure is not limited thereto.

In this embodiment, a use of the carbohydrate composition may be, for example, used to prepare a drug for inhibiting skin allergies, inhibiting skin inflammation, or improving atopic dermatitis without side effects. However, the disclosure is not limited thereto.

In this embodiment, the carbohydrate composition may be further used as an edible health food, a care product applied to skin, or a pharmaceutical ingredient, so as to nourish the skin, inhibit the skin allergies, inhibit the skin inflammation, or improve atopic dermatitis. In addition, the carbohydrate composition in this embodiment does not cause the side effects to a user or a patient. For example, the use of the carbohydrate composition in this embodiment may be, for example, used to prepare the health food or care product for nourishing the skin without side effects. However, the disclosure is not limited thereto. A use of the pharmaceutical ingredient in this embodiment may be, for example, used to prepare a drug that inhibits the skin allergies, inhibits the skin inflammation, or improves atopic dermatitis without side effects. However, the disclosure is not limited thereto.

The pharmaceutical ingredient in this embodiment may include the carbohydrate composition and the additive. The additive may include an excipient, a solvent, a diluent, a pigment, a flavoring agent, and/or a thickener, etc., as an inactive ingredient in the pharmaceutical ingredient. In this embodiment, the additive is not particularly limited, and may be adjusted according to the types or dosage forms of different pharmaceutical ingredients.

Regarding the application and efficacy of the carbohydrate composition and the pharmaceutical ingredient in the embodiment of the disclosure, the following embodiments with reference to the accompanying drawings are exemplary. However, the following embodiments and accompanying drawings are merely for auxiliary illustrations, and are not intended to limit the scope of the disclosure.

EMBODIMENT

Statistical analysis results in the following embodiments are all denoted by letters in the corresponding diagrams. The letters are, for example, a, b, c, d, e, f, etc. However, the disclosure is not limited thereto. When two groups in the diagram are marked with the same letter, it indicates that there is no significant difference between the two groups. On the contrary, when the two groups in the diagram are marked with different letters, it indicates that there is a significant difference between the two groups, and a p-value is less than 0.05. For example, when the first group is marked as a; the second group is marked as b; the third group is marked as bc, and the fourth group is marked as c, it may indicate that there is a significant difference between the first group (i.e., a) and the second group (i.e., b); there is no significant difference between the second group (i.e., b) and the third group (i.e., bc), and there is no significant difference between the third group (i.e., bc) and the fourth group (i.e., c).

Embodiment 1

A Component Analysis of the Carbohydrate Composition

First, 3 different batches of carbohydrate compositions are prepared, which are respectively Example 1, Example 2, and Example 3. The carbohydrate composition is, for example, the cladosiphon okamuranus extract as an example for illustration. However, the disclosure is not limited thereto. That is to say, in other embodiments, the carbohydrate composition may also be the carbohydrate mixture formed by compounding and mixing fucose, glucuronic acid, galactose, arabinose, and the other carbohydrates.

In this embodiment, a preparation method of the cladosiphon okamuranus extract includes the following steps. However, the disclosure is not limited thereto. At a specific pH value, temperature, and extraction time, an extractive reaction is performed on cladosiphon okamuranus with hot water and hydrochloric acid (HCl). Then, after centrifugation, ultrafiltration, and concentration, a neutralization reaction is performed with sodium hydroxide (NaOH) to the specific pH value. Next, an ultra-high temperature heating process is used to perform sterilization. At the specific temperature and rotation speed, an atomizer is used to perform spray drying. Afterwards, a vibration sifter and a screening size of 80 mesh is used to perform screening, so as to obtain the cladosiphon okamuranus extract.

Then, a nuclear magnetic resonance (NMR) method is used to analyze compositions of the carbohydrate compositions in Example 1, Example 2, and Example 3 and contents thereof, and analysis results thereof are shown in Table 1 below.

TABLE 1

|  | Example 1 | Example 2 | Example 3 |
|---|---|---|---|
| Fucose (% by weight) | 68.9 | 52.3 | 61 |
| Glucuronic acid (% by weight) | 11.8 | 16.2 | 16.6 |

TABLE 1-continued

|  | Example 1 | Example 2 | Example 3 |
|---|---|---|---|
| Galactose (% by weight) | 6.8 | 13.1 | 8.6 |
| Arabinose (% by weight) | 9.1 | 15.1 | 10.9 |
| Other carbohydrates (% by weight) | 3.4 | 3.3 | 2.9 |

Embodiment 2

An Effect on Cytotoxicity of the Carbohydrate Composition to RAW264.7 macrophages and Production of Nitric Oxide First, a solvent is used to formulate the carbohydrate composition into the carbohydrate compositions of different concentrations, that is, the carbohydrate compositions with concentrations of 31.25 μg/mL, 62.5 μg/mL, 125 μg/mL, 250 μg/mL, 500 μg/mL, and 1000 μg/mL. The solvent is, for example, phosphate buffered saline (PBS), but the disclosure is not limited thereto.

Then, $2 \times 10^5$ RAW264.7 macrophages are cultured in each well of a 96-well plate. After cultured in an incubator with 5% $CO_2$ at 37° C. for 30 minutes to allow the cells to attach, referring to FIGS. 1A to 1B, the carbohydrate compositions of different concentrations are added according to the groups, while lipopolysaccharide (LPS) of 1 μg/mL is also added according to the groups. LPS may stimulate or induce the macrophages to produce nitric oxide and cause inflammatory symptoms. After placed in the incubator and cultured for about 24 hours (that is, after a drug processing), the cytotoxicity of the carbohydrate composition to the macrophages is evaluated by counting the number of the cells, and the production of nitric oxide is evaluated by measuring a content of nitrite. Since nitric oxide is extremely unstable in the air and easily becomes nitrite and nitrate, a content of nitric oxide is evaluated by measuring the content of nitrite.

Specifically, a method of evaluating the cytotoxicity of the carbohydrate composition to the macrophages is, for example, that after the drug processing, the cells in each well are collected to respectively calculate the number of the cells. Next, the number of the cells in the group where the carbohydrate composition and lipopolysaccharide are not added is regarded as a cell survival rate of 100%, and the numbers of the cells in the other groups are respectively converted into the corresponding cell survival rate. In this way, the cytotoxicity of the carbohydrate composition to the macrophages is determined, and the result thereof are shown in FIG. 1A. It may be seen from the results in FIG. 1A that as the concentration of the added carbohydrate composition increases, there is no significant difference in the cell survival rate between different groups, which are all above 90%. Therefore, it may indicate that the carbohydrate composition does not cause the cytotoxicity to the macrophages.

In addition, a method of evaluating the production of nitric oxide is, for example, that after the drug processing, a supernatant of 50 μL is aspirated to an ELISA plate, and then Griess reagent A of 25 μL and Griess reagent B of 25 μL are added. After reaction in the dark, an absorbance value at 550 nm is tested, and a result thereof is shown in FIG. 1B.

Figure 1B:
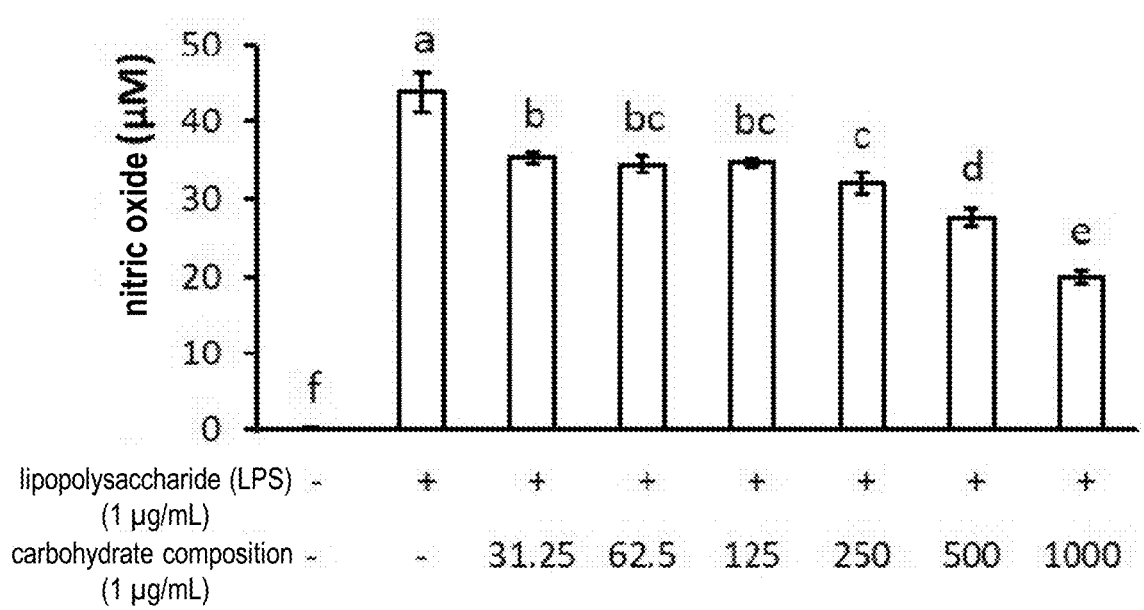

It may be seen form the result in FIG. 1B that compared with the group (the negative control group) without LPS added in which there is almost no production of nitric oxide, the group (the induction group) where LPS is added but no carbohydrate composition is added produces nitric oxide of about 45 μM. Compared with the group where LPS is added but no carbohydrate composition is added, the groups (the experimental groups) where both LPS and the carbohydrate composition (31.25 µg/mL, 62.5 µg/mL, 125 µg/mL, 250 µg/mL, 500 µg/mL, and 1000 µg/mL) are added may significantly inhibit the production of nitric oxide. In all the groups where both LPS and the carbohydrate composition are added, as the concentration of the added carbohydrate composition increases, the production of nitric oxide is more significantly inhibited. Therefore, it may indicate that the carbohydrate composition may inhibit the inflammatory symptoms by inhibiting the production of nitric oxide due to LPS stimulation.

Embodiment 3

An Effect of the Carbohydrate Composition on Degranulation of P815 Mast Cells, Interleukin-4, and Histamine First, the solvent is used to formulate the carbohydrate composition into the carbohydrate compositions of different concentrations, that is, the carbohydrate compositions with concentrations of 75 µg/mL, 150 µg/mL, 300 µg/mL, and 600 µg/mL. The solvent is, for example, PBS, but the disclosure is not limited thereto.

Then, $1 \times 10^6$ P815 mast cells are cultured in each well of a 24-well plate. After cultured in the incubator with 5% $CO_2$ at 37° C. for 1 hour to allow the cells to attach, referring to FIGS. 2A to 2C, the carbohydrate compositions of different concentrations are added according to the groups, while a mast cell degranulation agent (compound 48/80) of 10 µg/mL is also added according to the groups. The mast cell degranulation agent may induce degranulation of mast cells and release inflammatory mediators such as histamine to cause the inflammatory symptoms. After placed in the incubator and cultured for about 6 hours (that is, after the drug processing), the supernatant is aspirated to the ELISA plate to measure contents of interleukin-4 (IL-4) and histamine, and results thereof are shown in FIGS. 2B and 2C. Next, toluidine blue is used to stain the mast cells, so as to observe the degranulation of the mast cells, and results thereof are shown in FIG. 2A.

Figure 2A:
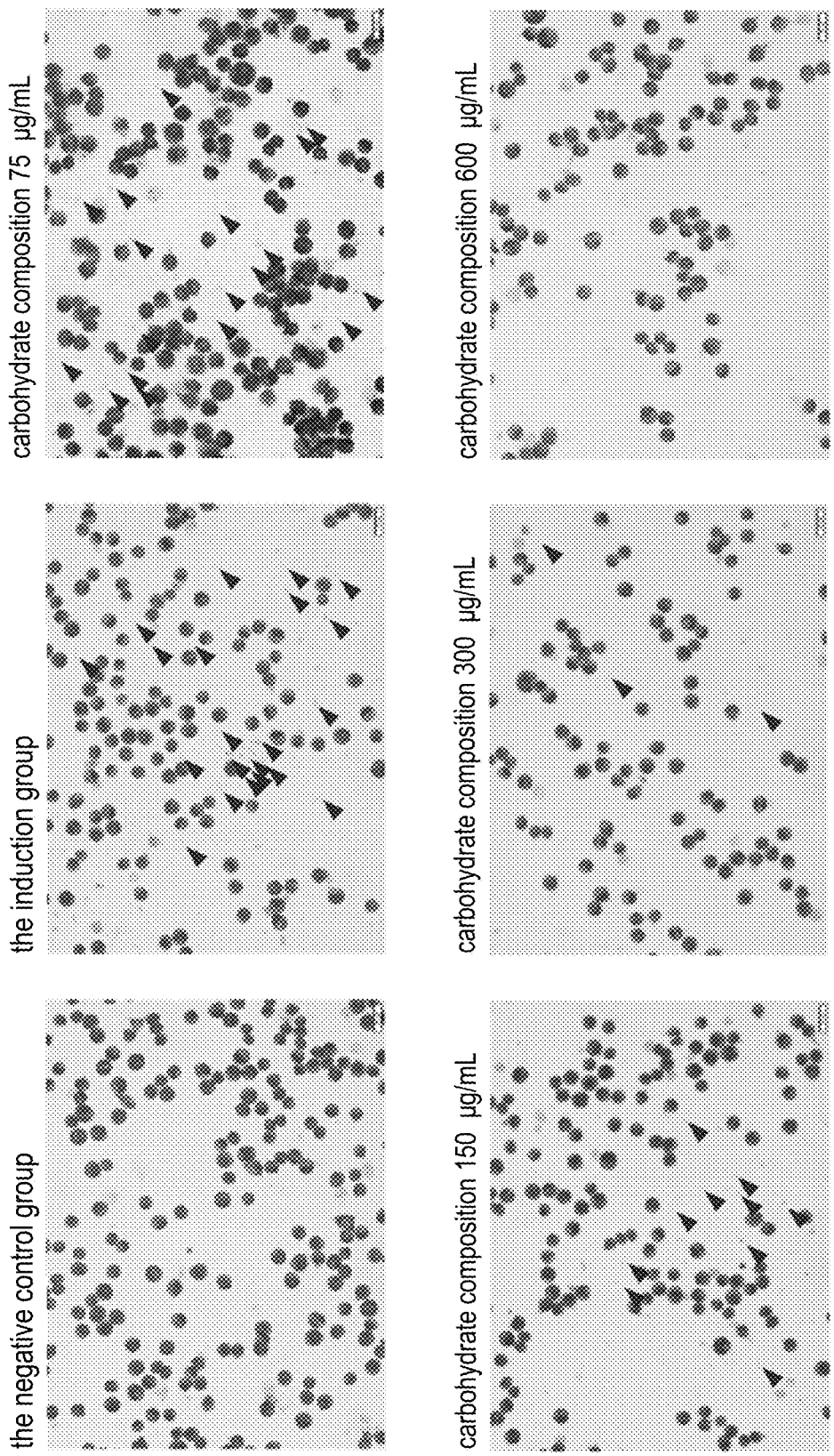
FIGS. 2A to 2C show an effect of the carbohydrate composition in this embodiment on degranulation of P815 mast cells, interleukin-4, and histamine.
Figure 2B:
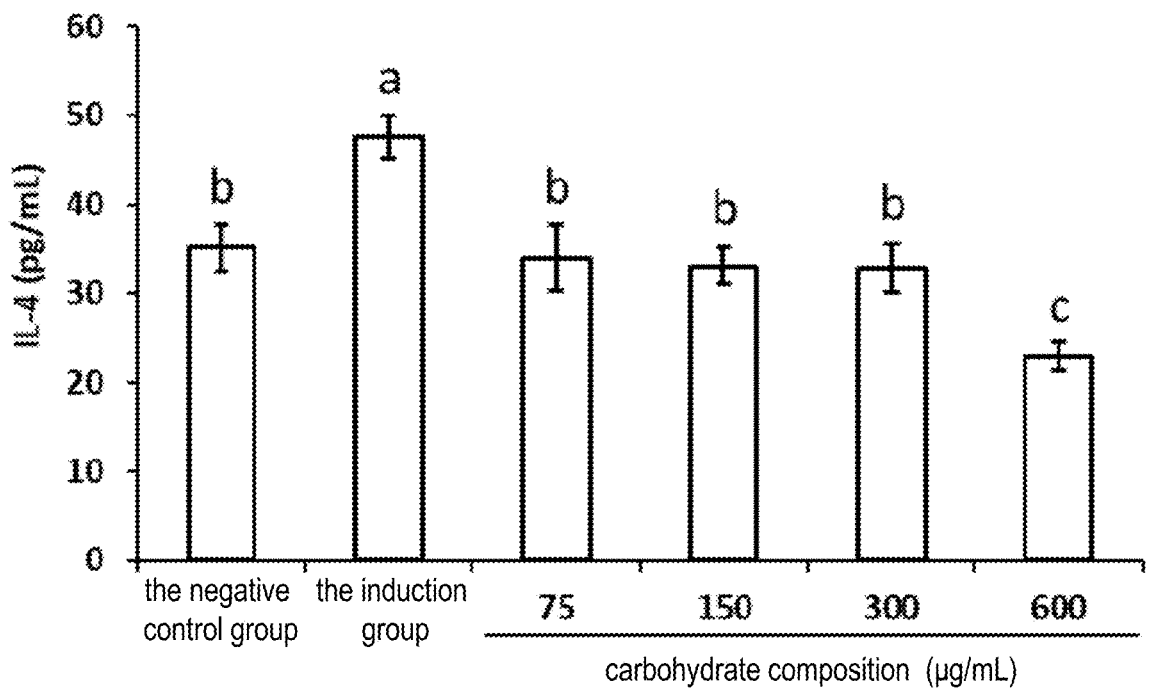
Figure 2C:
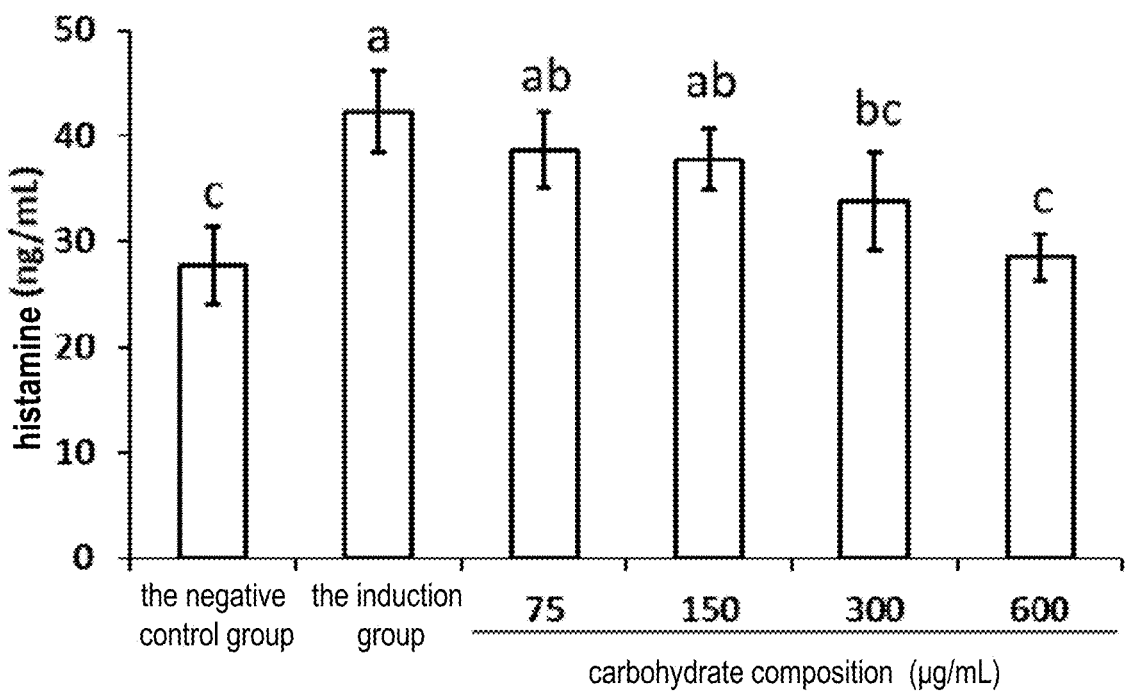

It may be seen from the results in FIG. 2A that compared with the group (the negative control group) where the mast cell degranulation agent is not added, multiple cases of the degranulation may be observed in the group (the induction group) where the mast cell degranulation agent is added but no carbohydrate composition is added, as shown by tips of triangles in FIG. 2A. Compared with the group (the induction group) where the mast cell degranulation agent is added but no carbohydrate composition is added, the groups (the experimental groups) where both the mast cell degranulation agent and the carbohydrate compositions (75 µg/mL, 150 µg/mL, 300 µg/mL, and 600 µg/mL) are added may significantly reduce the degranulation. In all the groups (the experimental groups) where both the mast cell degranulation agent and the carbohydrate composition are added, as the concentration of the added carbohydrate composition increases, the degranulation is more significantly reduced. Therefore, it may indicate that the carbohydrate composition may inhibit the degranulation of the mast cells.

It may be seen from the results in FIGS. 2B and 2C that compared with the group (the negative control group) where the mast cell degranulation agent is not added, the group (the induction group) where the mast cell degranulation agent is added but no carbohydrate composition is added may significantly increase the contents of IL-4 and histamine. Compared with the group (the induction group) where the mast cell degranulation agent is added but no carbohydrate composition is added, the groups (the experimental groups) where both the mast cell degranulation agent and the carbohydrate compositions (75 µg/mL, 150 µg/mL, 300 µg/mL, and 600 µg/mL) are added may significantly reduce the contents of IL-4 and histamine. In all the groups (the experimental groups) where both the mast cell degranulation agent and the carbohydrate composition are added, as the concentration of the added carbohydrate composition increases, the contents of IL-4 and histamine also decrease significantly. Therefore, it may indicate that the carbohydrate composition may inhibit IL-4 and histamine produced by the mast cells due to the degranulation, thereby inhibiting the inflammatory symptoms.

Embodiments 4 to 8

Figure 3:
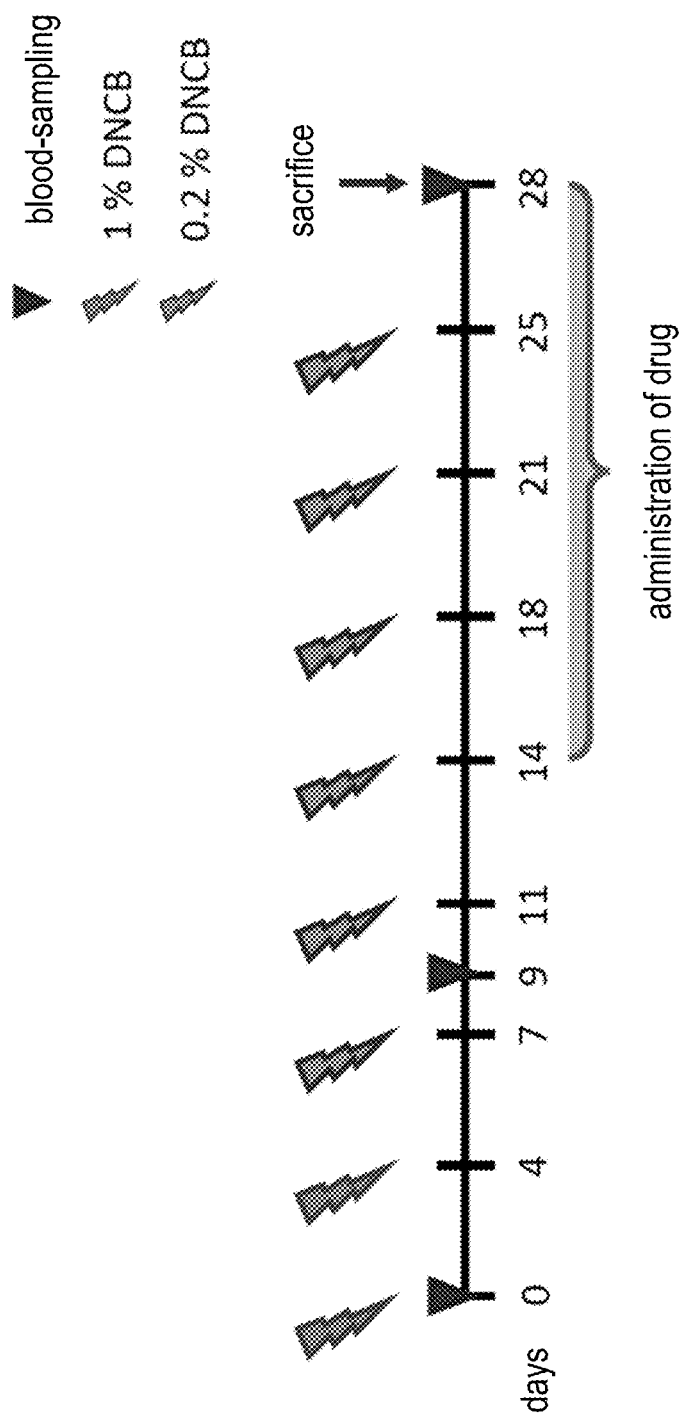
FIG. 3 is an experimental procedure of using a topical preparation or/and an oral preparation containing the carbohydrate composition in this embodiment to treat a mouse with atopic dermatitis.

Using the Topical Preparation Containing the Carbohydrate Composition to Treat a Mouse with Atopic Dermatitis First, referring to FIG. 3, a 1-chloro-2,4-dinitrobenzene (DNCB) solution is used as an inducer, and on days 0 and 4, DNCB of 1% is administered to back skin of a BALB/c male mouse aged 6 weeks, so as to sensitize the mouse to develop the allergic or inflammatory symptoms such as atopic dermatitis. Next, on days 7, 11, 14, 18, 21, and 25, DNCB of 0.2% is continuously administered to the mouse, so as to continuously challenge the mouse to develop the allergic or inflammatory symptoms such as atopic dermatitis. Then, on days 14 to 28, the drug such as Dermovate or the topical preparation (for example, the cream) is applied to an affected part of the skin every day. On days 0, 9, and 28, blood-sampling is performed to monitor a content of IgE in serum. On day 28, the mouse is sacrificed, and its blood, subiliac lymph nodes, skin, etc. are collected for subsequent analysis.

In addition, in this embodiment, as shown in FIGS. 4, 5, 6A to 6C, 7A to 7B, and 8, the mice are divided into 5 groups, and each group has 5 mice, which are respectively a negative control group, an induction group, a positive control group, a low-dose group, and a high-dose group. The negative control group is the group where DNCB and the topical preparation are not administered. The induction group is the group where DNCB is administered, but no topical preparation is administered. The positive control group is the group where DNCB and Dermovate are administered. The low-dose group is the group where DNCB and the topical preparation containing the carbohydrate composition of 35 mg/mL are administered. The high-dose group is the group where DNCB and the topical preparation containing the carbohydrate composition of 70 mg/mL are administered. DNCB is a commonly used composition for inducing animal models of atopic dermatitis. Dermovate is a commercially available ointment or cream containing clobetasol propionate (corticosteroids) of 0.05% by weight, which may be applied to the affected part and used to treat skin diseases such as atopic dermatitis.

Embodiments 4

An Effect of Using the Topical Preparation on a Dermatitis Score of the Mouse with Atopic Dermatitis First, it is scored by unaided viewing and a dermatitis score of atopic dermatitis to determine the severity of atopic dermatitis and the condition of skin recovery. The symptoms of skin allergies and skin inflammation caused by atopic dermatitis may include erythema/hemorrhage, scaring/dryness, edema, and excoriation/erosion. A scoring standard is 0 to 3 points, where 0 point indicates no symptoms; 1 point indicates mild symptoms; 2 points indicate moderate symptoms, and 3 points indicates severe symptoms. Next, on days 4, 7, 11, 14, 18, 21, 25, and 28, the mice in each group are scored by the dermatitis score of atopic dermatitis, and a result thereof is shown in FIG. 4.

Figure 4:
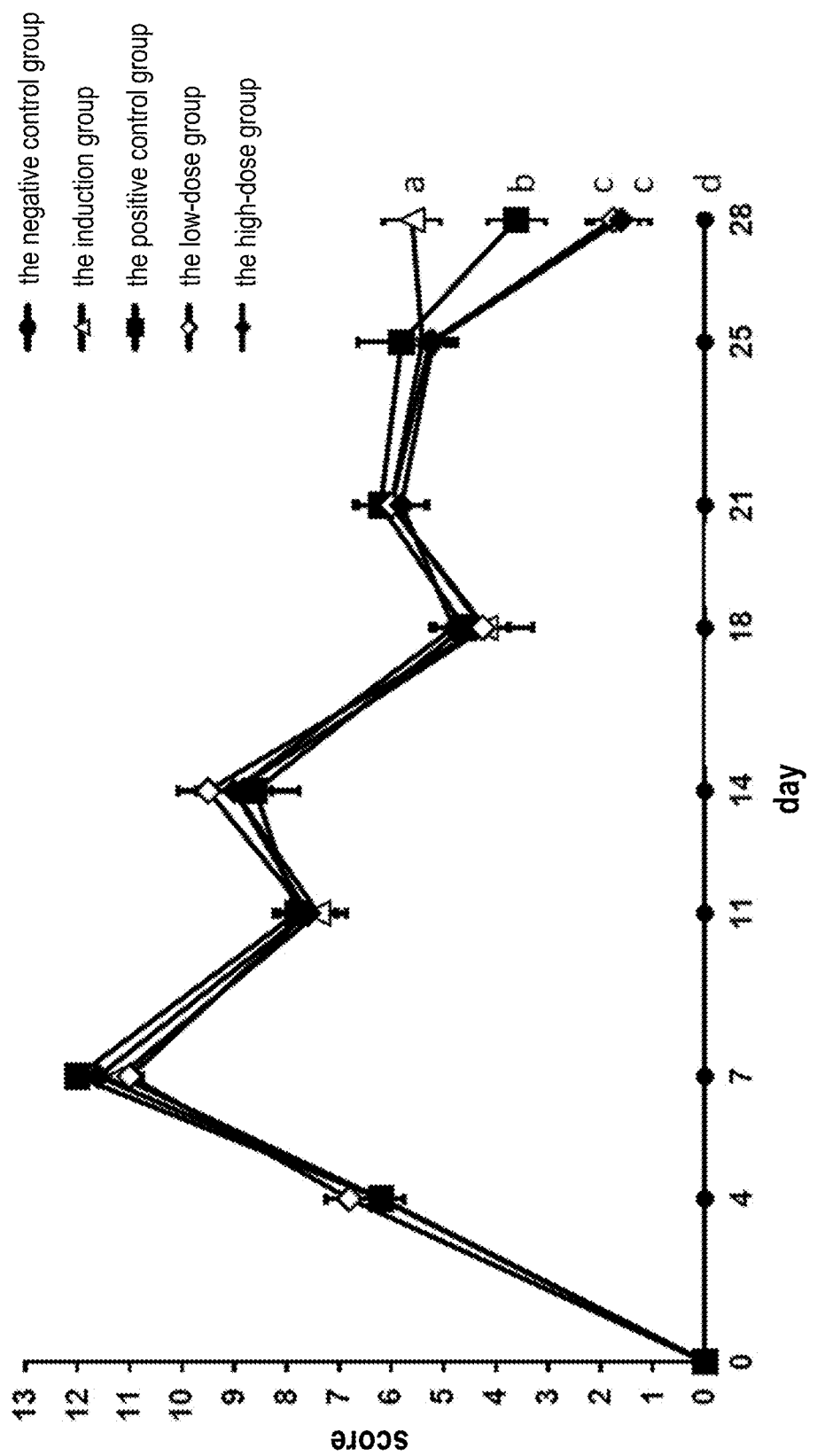
FIG. 4 shows an effect of using the topical preparation in this embodiment on a dermatitis score of the mouse with atopic dermatitis.

It may be seen form the result in FIG. 4 that compared with the negative control group where DNCB and the topical preparation are not administered, the induction group where DNCB is administered but no topical preparation is administered has significantly higher scores and more severe symptoms of skin allergies and skin inflammation. Compared with the induction group where DNCB is administered but no topical preparation is administered, the positive control group where DNCB and Dermovate are administered, the low-dose group where DNCB and the topical preparation containing the carbohydrate composition of 35 mg/mL are administered, and the high-dose group where DNCB and the topical preparation containing the carbohydrate composition of 70 mg/mL are administered may significantly reduce the scores and alleviate the symptoms of skin allergies and skin inflammation. Compared with the positive control group where DNCB and Dermovate are administered, the low-dose group and the high-dose group where DNCB and the topical preparation containing the carbohydrate composition are administered have better effects to alleviate the symptoms of skin allergies and skin inflammation. Therefore, it may indicate that the topical preparation containing the carbohydrate composition may be targeted at a lesion to inhibit the symptoms of skin allergies and skin inflammation, thereby repairing the skin and improving or treating atopic dermatitis.

Embodiments 5

An Effect of Using the Topical Preparation on Subiliac Lymph Nodes of the Mouse with Atopic Dermatitis Atopic dermatitis often causes inflammation of the subiliac lymph nodes, which leads to the swollen subiliac lymph nodes. Therefore, in the following, the severity of atopic dermatitis is determined by measuring weight of the subiliac lymph nodes of the mice in each group, and a result thereof is shown in FIG. 5.

Figure 5:
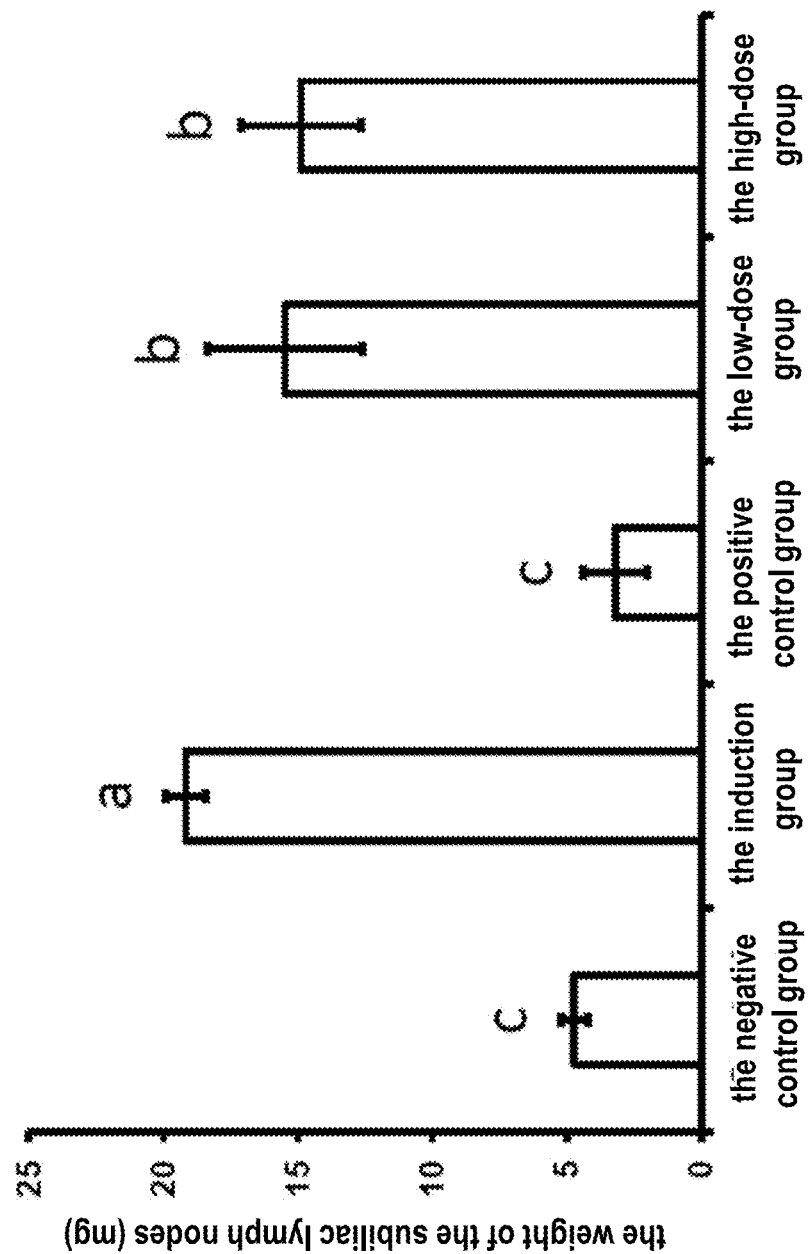
FIG. 5 shows an effect of using the topical preparation in this embodiment on subiliac lymph nodes of the mouse with atopic dermatitis.

It may be seen from the result in FIG. 5 that compared with the negative control group where DNCB and the topical preparation are not administered, the induction group where DNCB is administered but no topical preparation is administered has significantly heavier subiliac lymph nodes. Compared with the induction group where DNCB is administered but no topical preparation is administered, the positive control group where DNCB and Dermovate are administered, the low-dose group where DNCB and the topical preparation containing the carbohydrate composition of 35 mg/mL are administered, and the high-dose group where DNCB and the topical preparation containing the carbohydrate composition of 70 mg/mL are administered may significantly reduce the weight of the subiliac lymph nodes. Therefore, it may indicate that the topical preparation containing the carbohydrate composition may be targeted at the lesion to reduce inflammation and swelling of the subiliac lymph nodes, thereby improving or treating atopic dermatitis.

Embodiments 6

Figure 6A:
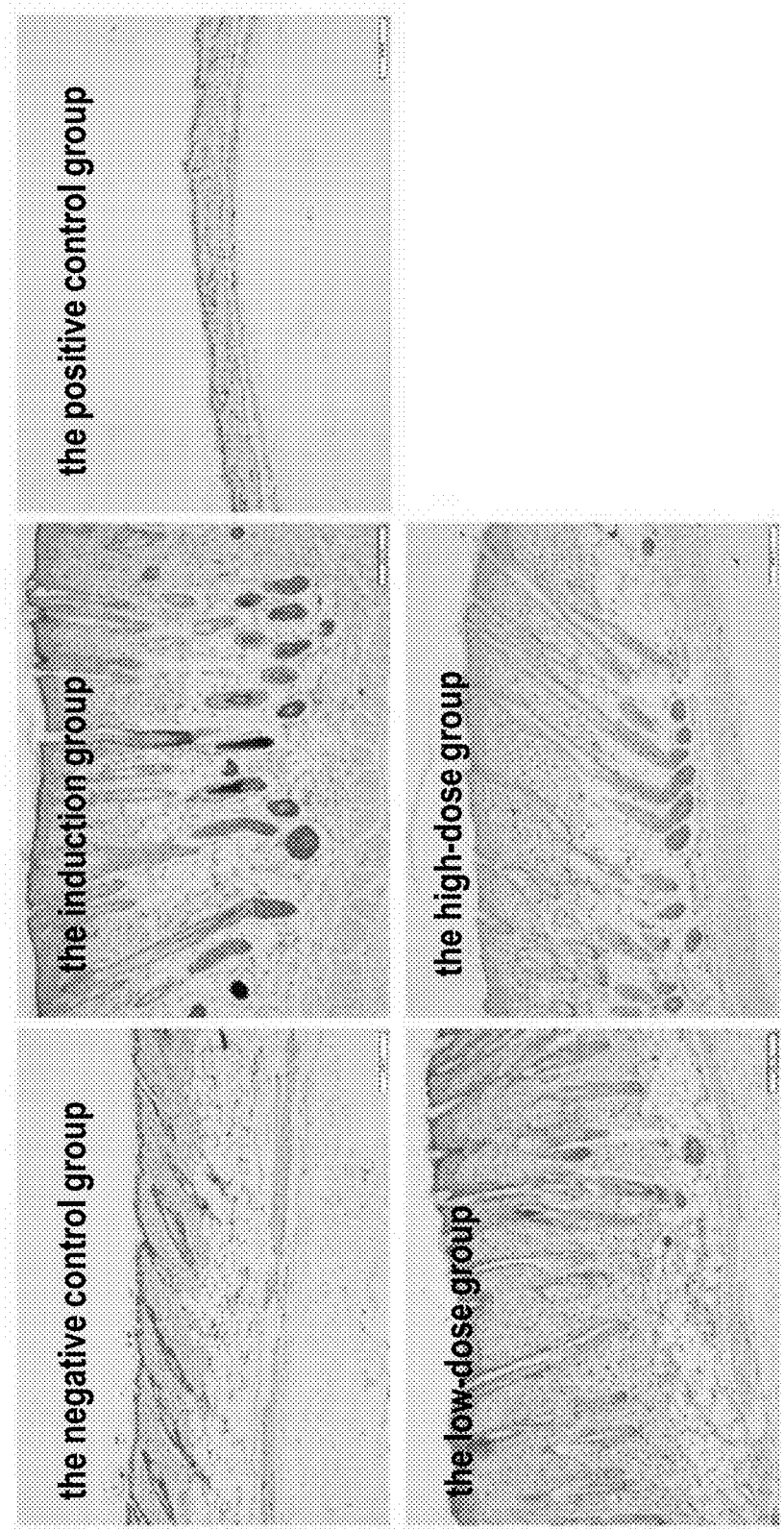
FIGS. 6A to 6C show an effect of using the topical preparation in this embodiment on a skin thickness of the mouse with atopic dermatitis.
Figure 6B:
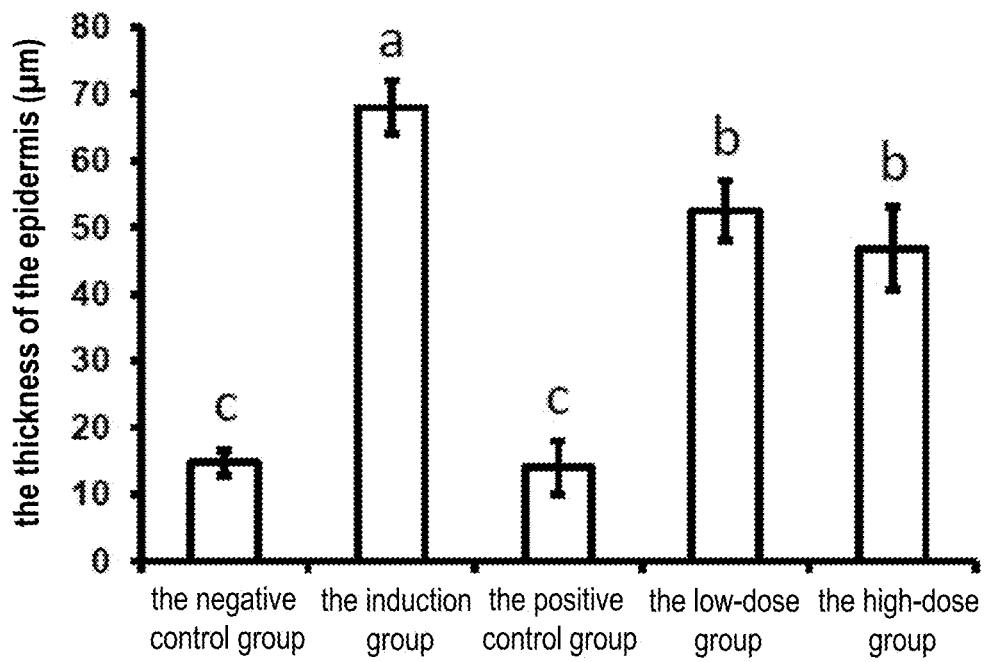
Figure 6C:
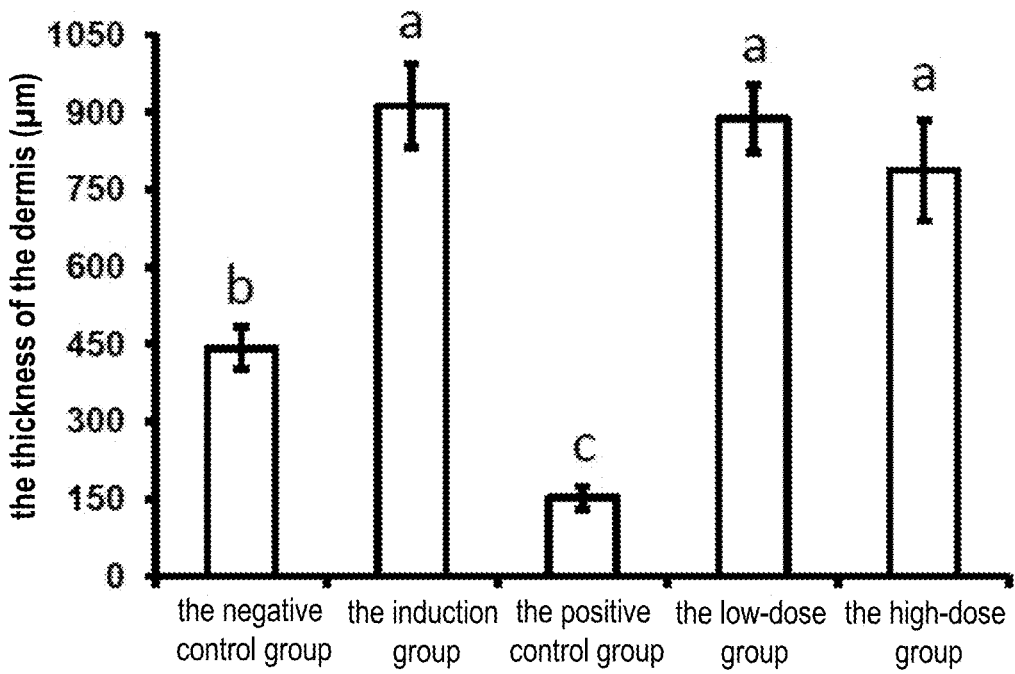

An Effect of Using the Topical Preparation on a Skin Thickness of the Mouse with Atopic Dermatitis H&E stain is performed on skin tissue of the mice in each group to observe and measure thickness changes in epidermis and dermis of the skin, and steps thereof are substantially as follows. Before staining, paraffin in the embedded tissue is dewaxed with xylene and covered with water. Then, slides are immersed in blue hematoxylin and stained for a few seconds, rinsed with running water until the water is colorless, and then stained with red eosin for a few seconds. The slides are rinsed with the running water, and after the slides are dried, the slides are immersed in ethanol of 70%, 90%, and 100% and xylene respectively for dehydration. Next, after the slides are dried, the slides may be mounted and stored, and staining results thereof are shown in FIGS. 6A to 6C. FIG. 6B is a quantization result of a thickness of the epidermis in FIG. 6A, and FIG. 6C is a quantization result of a thickness of the dermis in FIG. 6A.

It may be seen form the results in FIGS. 6A to 6C that compared with the negative control group where DNCB and the topical preparation are not administered, the induction group where DNCB is administered but no topical preparation is administered may significantly increase the thicknesses of the epidermis and the dermis. Compared with the induction group where DNCB is administered but no topical preparation is administered, the positive control group where DNCB and Dermovate are administered, the low-dose group where DNCB and the topical preparation containing the carbohydrate composition of 35 mg/mL are administered, and the high-dose group where DNCB and the topical preparation containing the carbohydrate composition of 70 mg/mL are administered may significantly reduce the thickness of the epidermis. Therefore, it may indicate that the topical preparation containing the carbohydrate composition may be targeted at the lesion to slow down thickening of the epidermis.

Embodiments 7

Figure 7A:
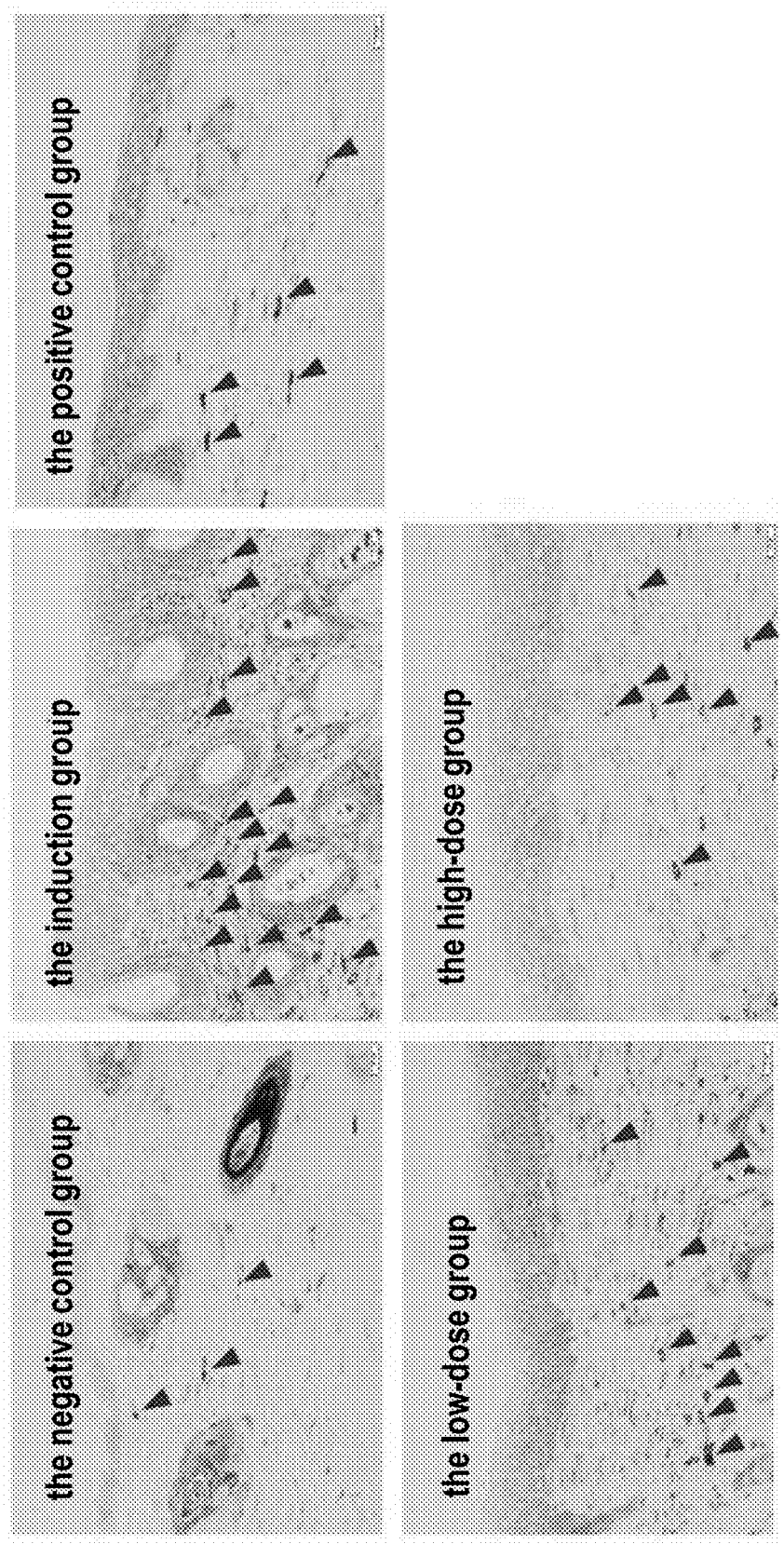
FIGS. 7A to 7B show an effect of using the topical preparation in this embodiment on skin lesions in the mouse with atopic dermatitis.
Figure 7B:
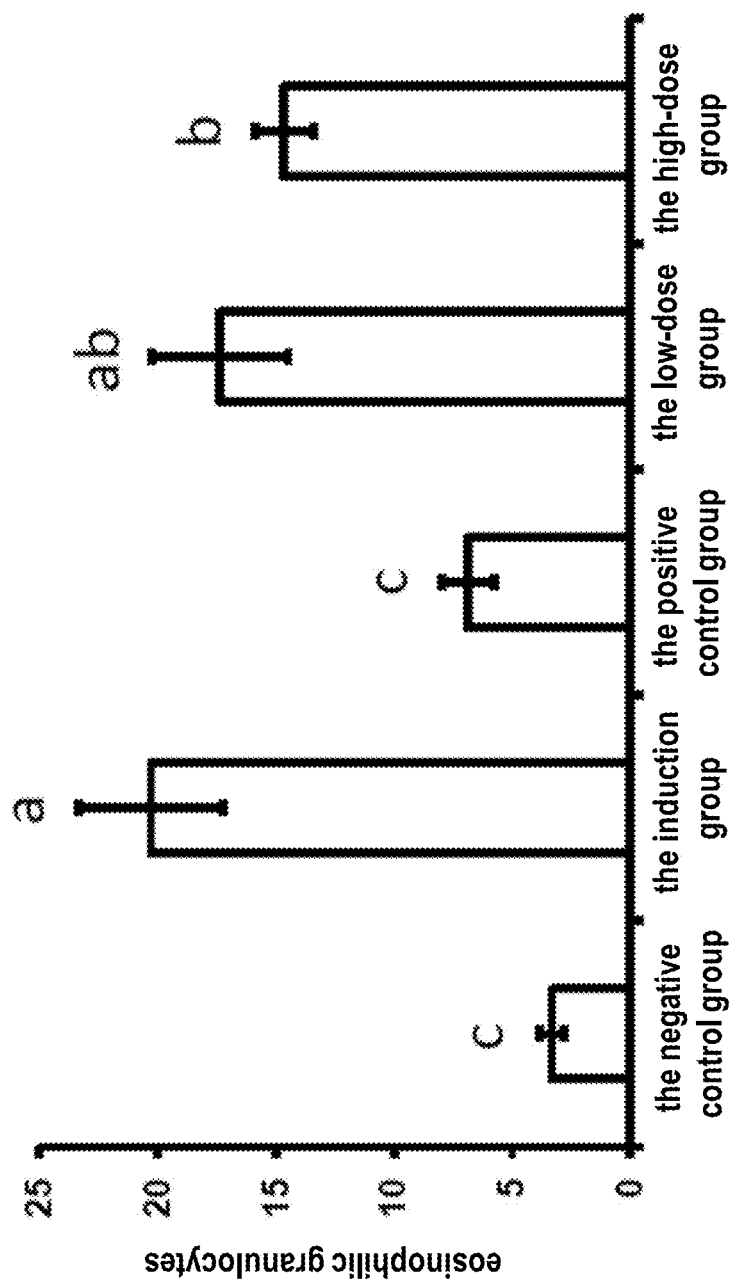

An Effect of Using the Topical Preparation on Skin Lesions in the Mouse with Atopic Dermatitis Giemsa stain is performed on the skin tissue of the mice in each group to observe and measure the skin lesions, and steps thereof are substantially as follows. Before staining, the paraffin covering the tissue is removed. After covering the slides with water, the slides are immersed in methanol to be fixed for 5 minutes. After the slides are air-dried, the slides are put into a 20-fold diluted Giemsa stain, rinsed with the running water after 40 minutes until the water is colorless. After the slides are air-dried, the slides are immersed in ethanol of 70%, 90%, and 100% and xylene respectively for dehydration. Next, after the slides are air-dried, the slides may be mounted and stored, and staining results thereof are shown in FIGS. 7A to 7B. FIG. 7B is a quantization result of eosinophilic granulocytes (as shown by the tips of the triangles in FIG. 7A) in FIG. 7A.

It may be seen form the results in FIGS. 7A to 7B that compared with the negative control group where DNCB and the topical preparation are not administered, the induction group where DNCB is administered but no topical preparation is administered may significantly increase infiltration of the eosinophilic granules into the dermis. Compared with the induction group where DNCB is administered but no topical preparation is administered, the positive control group where DNCB and Dermovate are administered, and the high-dose group where DNCB and the topical preparation containing the carbohydrate composition of 70 mg/mL are administered may significantly reduce the infiltration of eosinophilic granules in the dermis. Therefore, it may indicate that the topical preparation containing the carbohydrate composition may be targeted at the lesion to reduce the infiltration of eosinophilic granules in the dermis, thereby alleviating the skin lesions.

Embodiments 8

An Effect of Using the Topical Preparation on IgE in the Mouse with Atopic Dermatitis Atopic dermatitis may degranulate the mast cells through excessive secretion of immunoglobulin E (IgE), which leads to the symptoms of skin allergies and skin inflammation such as the release of histamine, the infiltration of eosinophilic granules, and the swollen subiliac lymph nodes. Therefore, in the following, the severity of atopic dermatitis is determined by measuring a content of IgE in the mice in each group.

Hereinafter, an Enzyme-linked immunosorbent assay (ELISA assay) is used to analyze the blood of the mice in each group sampled on days 0, 9, and 28, so as to measure the content of IgE in the blood, and steps thereof are substantially as follows. A commercially available Mouse ELISA ready-set-go kit is used for analysis. First, a capture antibody of 100 μL is fixed in wells of the ELISA plate, sealed, and placed at 4° C. to overnight. Then, after washing each well with a wash buffer of more than 250 μL 3 times, Blocking Buffer of 200 μL is added to actuate at a room temperature for 1 hour. After that, according to instructions, serial dilution is performed on the standard with ELISA/ELISPOT of 1×, and then the standards with different concentrations of 100 μL and serum of 100 μL to be tested are respectively added into different wells. After reacting at the room temperature for 2 hours, each well is washed 3 to 5 times with the wash buffer of more than 250 μL. Next, a detection antibody of 100 μL is added and reacts at the room temperature for 1 hour, and then each well is washed 3 to 5 times with the wash buffer of more than 250 μL. Avidin-HRP of 100 μL is added and reacts at the room temperature for 30 minutes. Then, each well is washed 5 to 7 times with the wash buffer of more than 250 μL, and then a 1×TMB solution of 100 μL is added. After reacting at the room temperature and protected from light for 15 minutes, a stop solution of 50 μL is added, and an absorbance thereof at a wavelength of 450 nm is measured, and a result is shown in FIG. 8.

Figure 8:
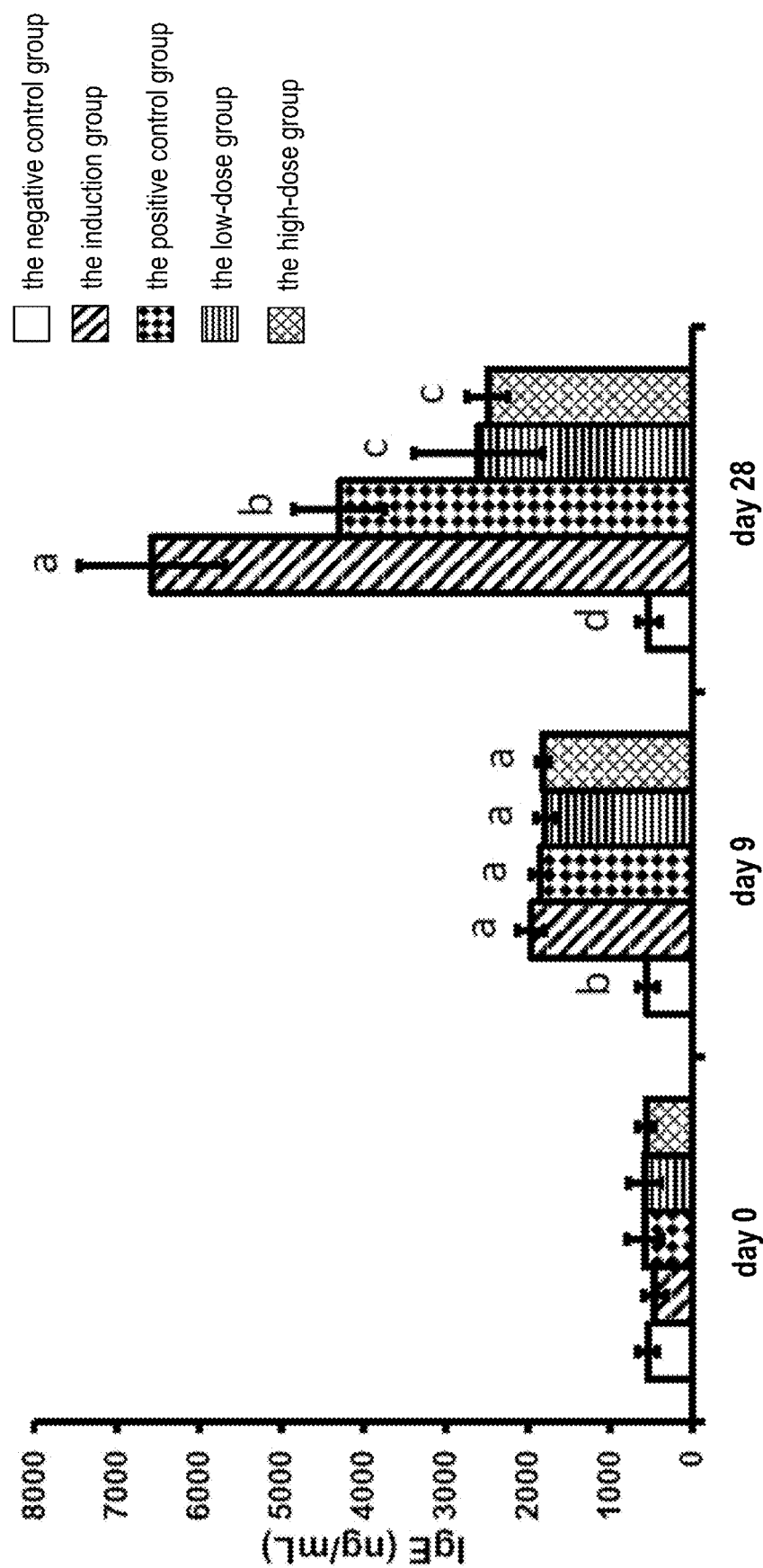
FIG. 8 shows an effect of using the topical preparation in this embodiment on IgE in the mouse with atopic dermatitis.

It may be seen form the result on day 9 in FIG. 8 that compared with the negative control group where DNCB and the topical preparation are not administered, the induction group where DNCB is administered, the positive control group where DNCB is administered, the low-dose group where DNCB is administered, and the high-dose group a where DNCB is administered may significantly increase the content of IgE due to induction of DNCB.

It may be seen form the result on day 28 in FIG. 8 that compared with the negative control group where DNCB is not administered, the induction group where DNCB is administered but no topical preparation is administered may significantly has higher content of IgE. Compared with the induction group where DNCB is administered but no topical preparation is administered, the positive control group where DNCB and Dermovate are administered, the low-dose group where DNCB and the topical preparation containing the carbohydrate composition of 35 mg/mL are administered, and the high-dose group where DNCB and the topical preparation containing the carbohydrate composition of 70 mg/mL are administered may significantly reduce the content of IgE. Compared with the positive control group where DNCB and Dermovate are administered, the low-dose group where DNCB and the topical preparation containing the carbohydrate composition of 35 mg/mL are administered, and the high-dose group where DNCB and the topical preparation containing the carbohydrate composition of 70 mg/mL are administered may more significantly reduce the content of IgE. Therefore, it may indicate that the topical preparation containing the carbohydrate composition may be targeted at the lesion to reduce the content of IgE, thereby improving or treating atopic dermatitis.

Embodiments 9 to 14

Using an Oral Preparation Containing the Carbohydrate Composition to Treat a Mouse with Atopic Dermatitis First, referring to FIG. 3, the mice with atopic dermatitis are prepared by the same or similar method as in Embodiments 4 to 8, and blood-sampling and sacrifice are performed at the same time point. However, a difference between Embodiments 9 to 14 and Embodiments 4 to 8 is that on days 14 to 28, gavage is performed with the oral preparation every day. In addition, in this embodiment, as shown in FIGS. 9, 10, 11A to 11B, 12A to 12B, 13A to 13B, and 14, the mice are divided into 6 groups, which are a negative control group, an induction group, and a positive control group, a low-dose group, a medium-dose group, and a high-dose group. The negative control group is the group where DNCB and the oral preparation are not administered. The induction group is the group where DNCB is administered but no oral preparation is administered. The positive control group is the group where DNCB and dexamethasone are administered. The low-dose group is the group where DNCB and the oral preparation containing the carbohydrate composition of 200 mg/kg are administered. The medium-dose group is the group where DNCB and the oral preparation containing the carbohydrate composition of 400 mg/kg are administered. The high-dose group is the group where DNCB and the oral preparation containing the carbohydrate composition of 800 mg/kg are administered. Dexamethasone is a commercially available synthetic corticosteroids, which may be used to treat the skin diseases such as atopic dermatitis.

Embodiment 9

Figure 9:
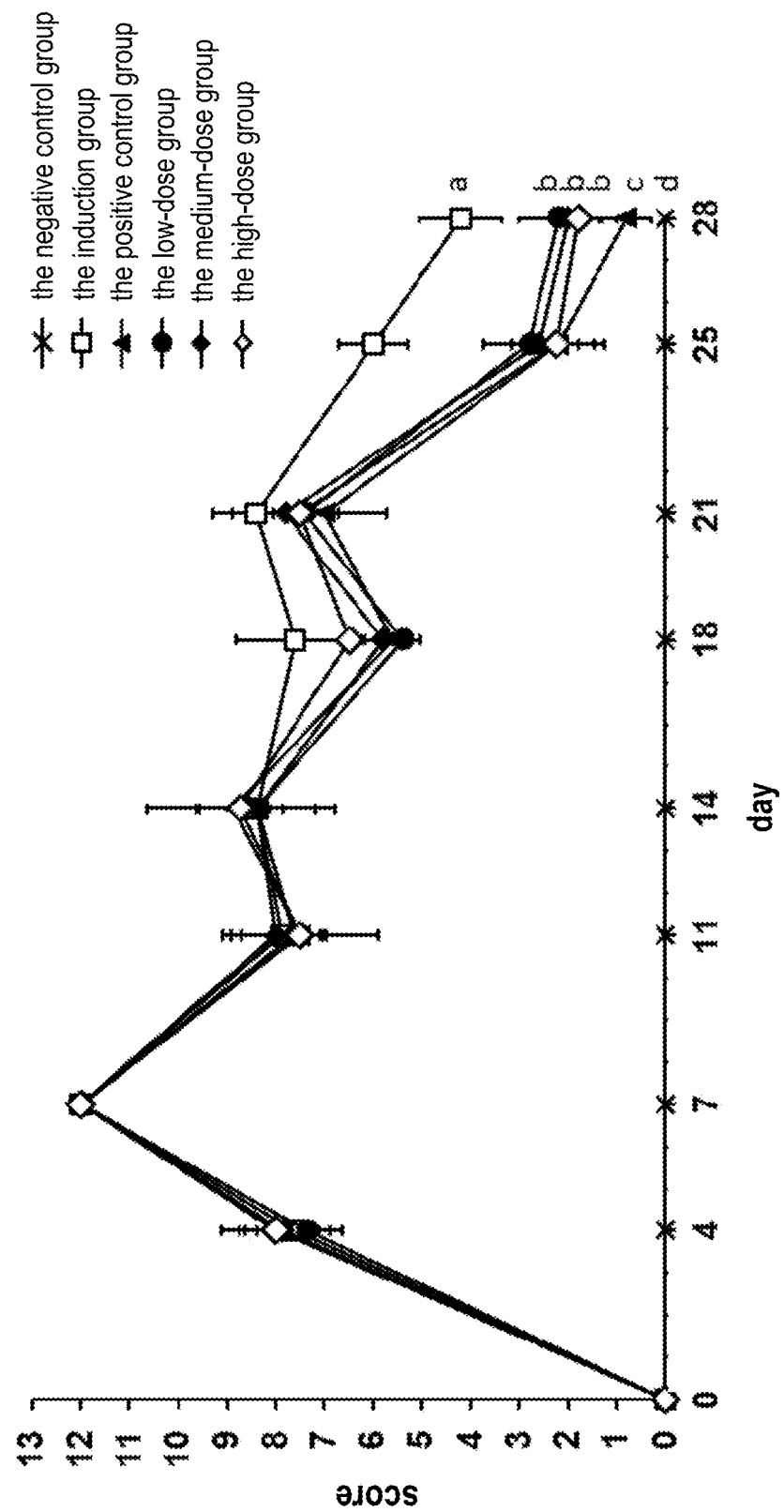
FIG. 9 shows an effect of using the oral preparation in this embodiment on the dermatitis score of the mouse with atopic dermatitis.

An Effect of Using the Oral Preparation on the Dermatitis Score of the Mouse with Atopic Dermatitis The severity of atopic dermatitis and the condition of skin recovery of the mice in each group are determined by the same or similar method as in Embodiment 4, and a result thereof is shown in FIG. 9.

It may be seen form the result in FIG. 9 that compared with the negative control group where DNCB and the oral preparation are not administered, the induction group where DNCB is administered but no oral preparation is administered has significantly higher scores and more severe symptoms of skin allergies and skin inflammation. Compared with the induction group where DNCB is administered but no oral preparation is administered, the positive control group where DNCB and dexamethasone are administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the scores and alleviate the symptoms of skin allergies and skin inflammation. Therefore, it may indicate that the oral preparation containing the carbohydrate composition may inhibit the symptoms of skin allergies and skin inflammation, thereby repairing the skin and improving or treating atopic dermatitis.

Embodiment 10

Figure 10:
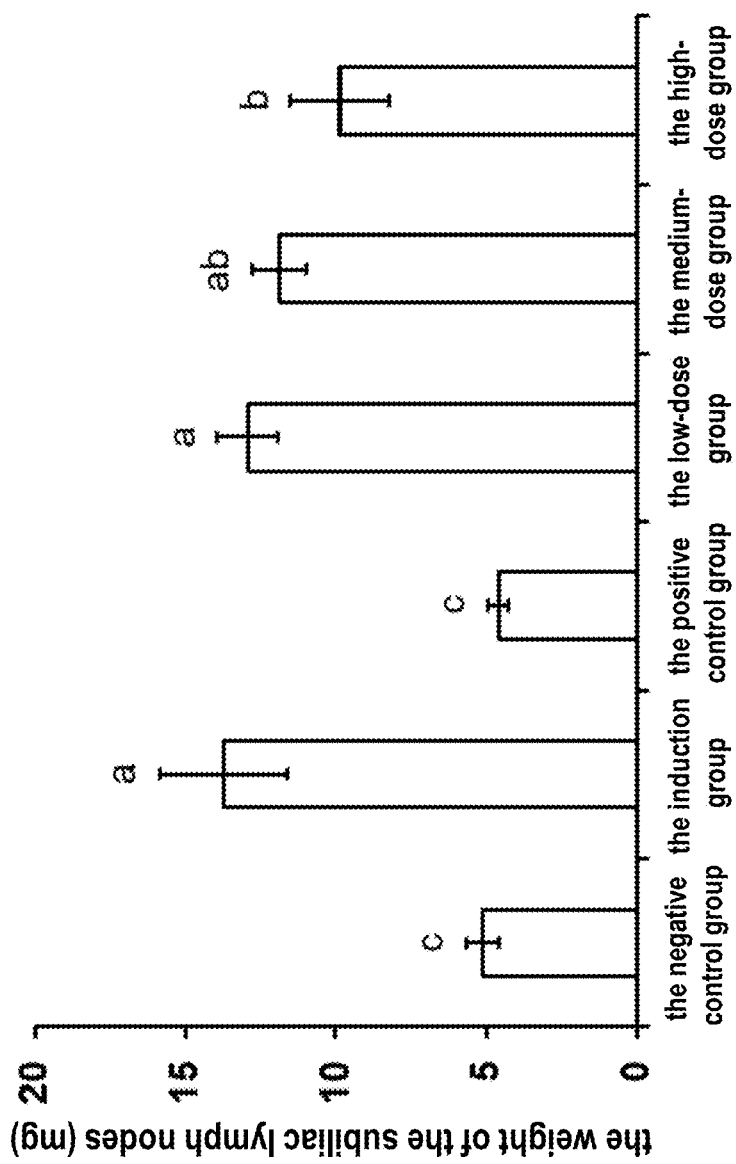
FIG. 10 shows an effect of using the oral preparation in this embodiment on the subiliac lymph nodes of the mouse with atopic dermatitis.

An Effect of Using the Oral Preparation on the Subiliac Lymph Nodes of the Mouse with Atopic Dermatitis The weight of the subiliac lymph nodes of the mice in each group is measured by the same or similar method as in Embodiment 5, and a result thereof is shown in FIG. 10.

It may be seen form the result in FIG. 10 that compared with the negative control group where DNCB and the oral preparation are not administered, the induction group where DNCB is administered but no oral preparation is administered has significantly heavier subiliac lymph nodes. Compared with the induction group where DNCB is administered but no oral preparation is administered, the positive control group where DNCB and dexamethasone are administered, and the high-dose group where DNCB and the oral preparation containing the carbohydrate composition of 800 mg/kg are administered may significantly reduce the weight of the subiliac lymph nodes. Therefore, it may indicate that the topical preparation containing the carbohydrate composition may reduce the inflammation and swelling of the subiliac lymph nodes, thereby improving or treating atopic dermatitis.

Embodiment 11

Figure 11A:
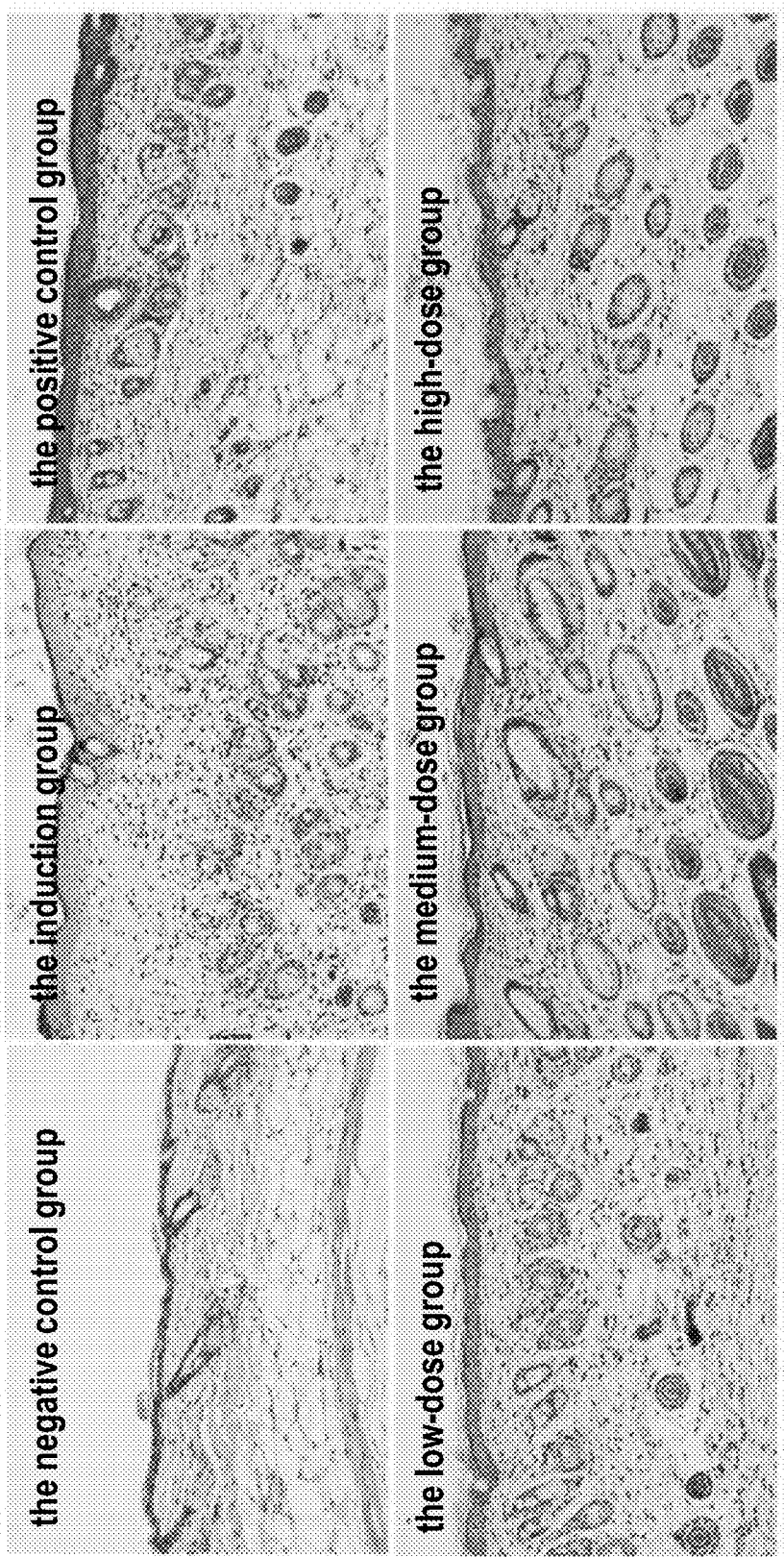
FIGS. 11A to 11B show an effect of using the oral preparation in this embodiment on the skin thickness of the mouse with atopic dermatitis.
Figure 11B:
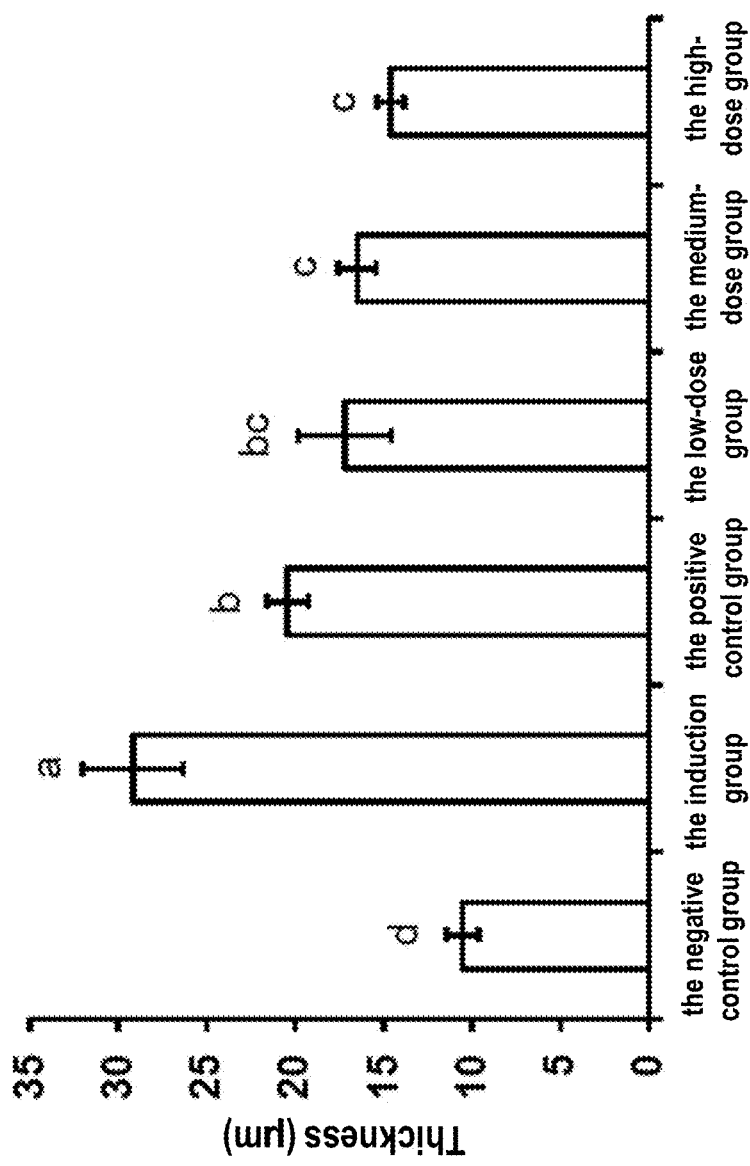

An Effect of Using the Oral Preparation on the Skin Thickness of the Mouse with Atopic Dermatitis The thickness changes in the epidermis and dermis of the skin are observed and measured by the same or similar method as in Embodiment 6, and results thereof are shown in FIGS. 11A and 11B. FIG. 11B is a quantization result of the thickness of the epidermis in FIG. 11A.

It may be seen form the results in FIGS. 11A and 11B that compared with the negative control group where DNCB and the oral preparation are not administered, the induction group where DNCB is administered but no oral preparation is administered may significantly increase the thickness of the epidermis. Compared with the induction group where DNCB is administered but no oral preparation is administered, the positive control group where DNCB and dexamethasone are administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the thickness of the epidermis. Therefore, it may indicate that the oral preparations containing the carbohydrate composition may slow down thickening of the epidermis.

Embodiment 12

Figure 12A:
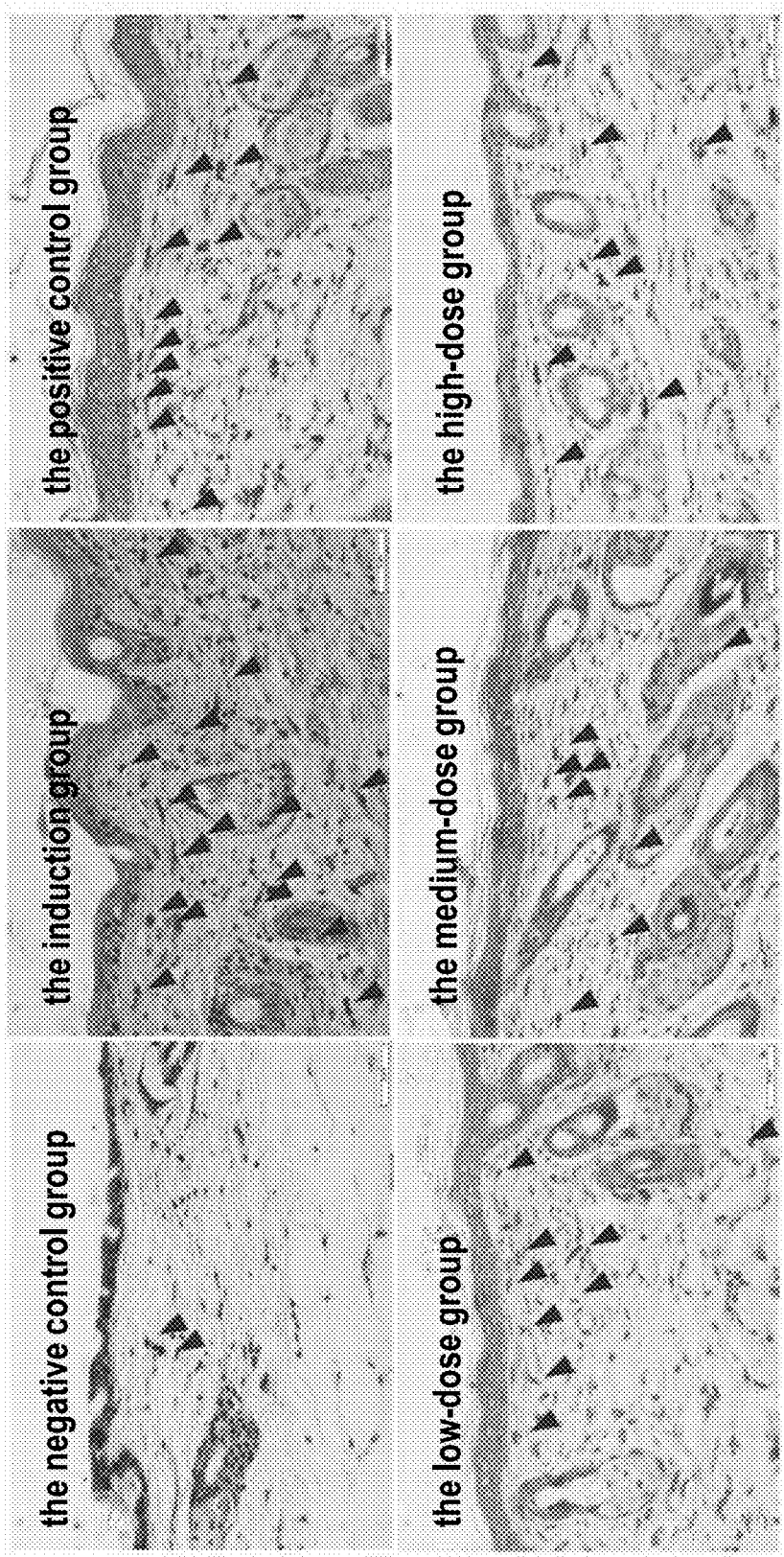
FIGS. 12A to 12B show an effect of using the oral preparation in this embodiment on the skin lesions in the mouse with atopic dermatitis.
Figure 12B:
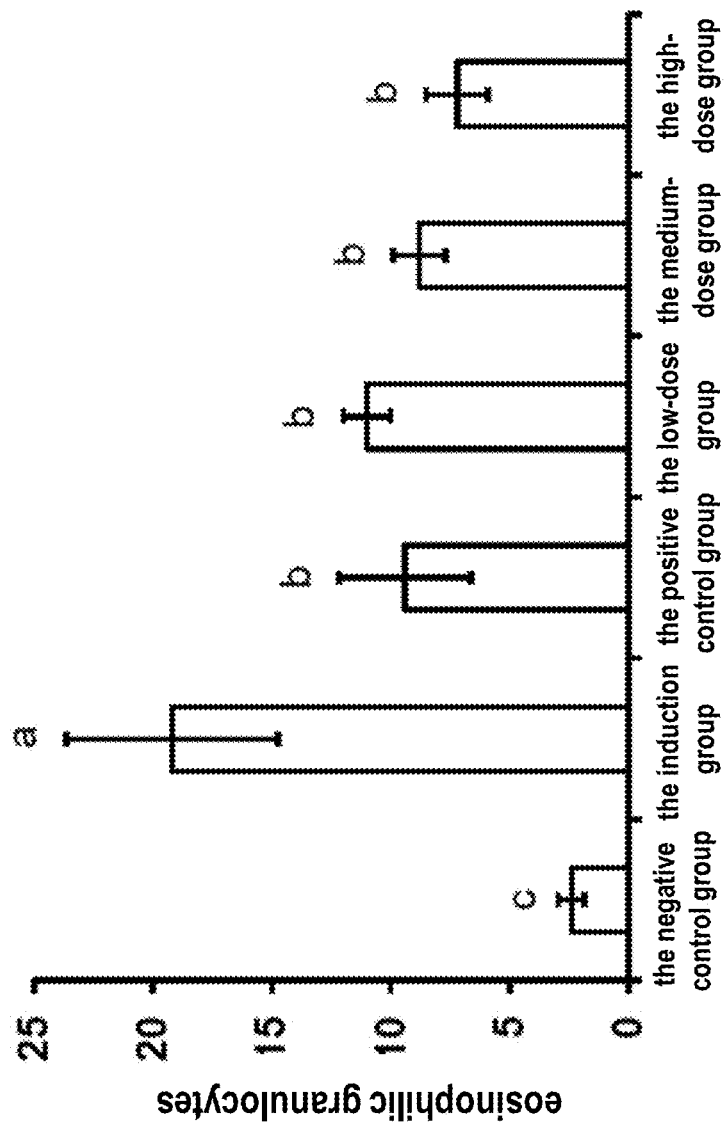

An Effect of Using the Oral Preparation on the Skin Lesions in the Mouse with Atopic Dermatitis The skin lesions in the mice in each group are observed and measured by the same or similar method as in Embodiment 7, and results thereof are shown in FIGS. 12A and 12B. FIG. 12B is a quantization result of eosinophilic granulocytes (as shown by the tips of the triangles in FIG. 12A) in FIG. 12A.

It may be seen form the results in FIGS. 12A and 12B that compared with the negative control group where DNCB and the oral preparation are not administered, the induction group where DNCB is administered but no oral preparation is administered may significantly increase infiltration of the eosinophilic granules into the dermis. Compared with the induction group where DNCB is administered but no oral preparation is administered, the positive control group where DNCB and dexamethasone are administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the infiltration of eosinophilic granules in the dermis. Therefore, it may indicate that the oral preparation containing the carbohydrate composition may reduce the infiltration of eosinophilic granules in the dermis, thereby alleviating the skin lesions.

Embodiment 13

Figure 13A:
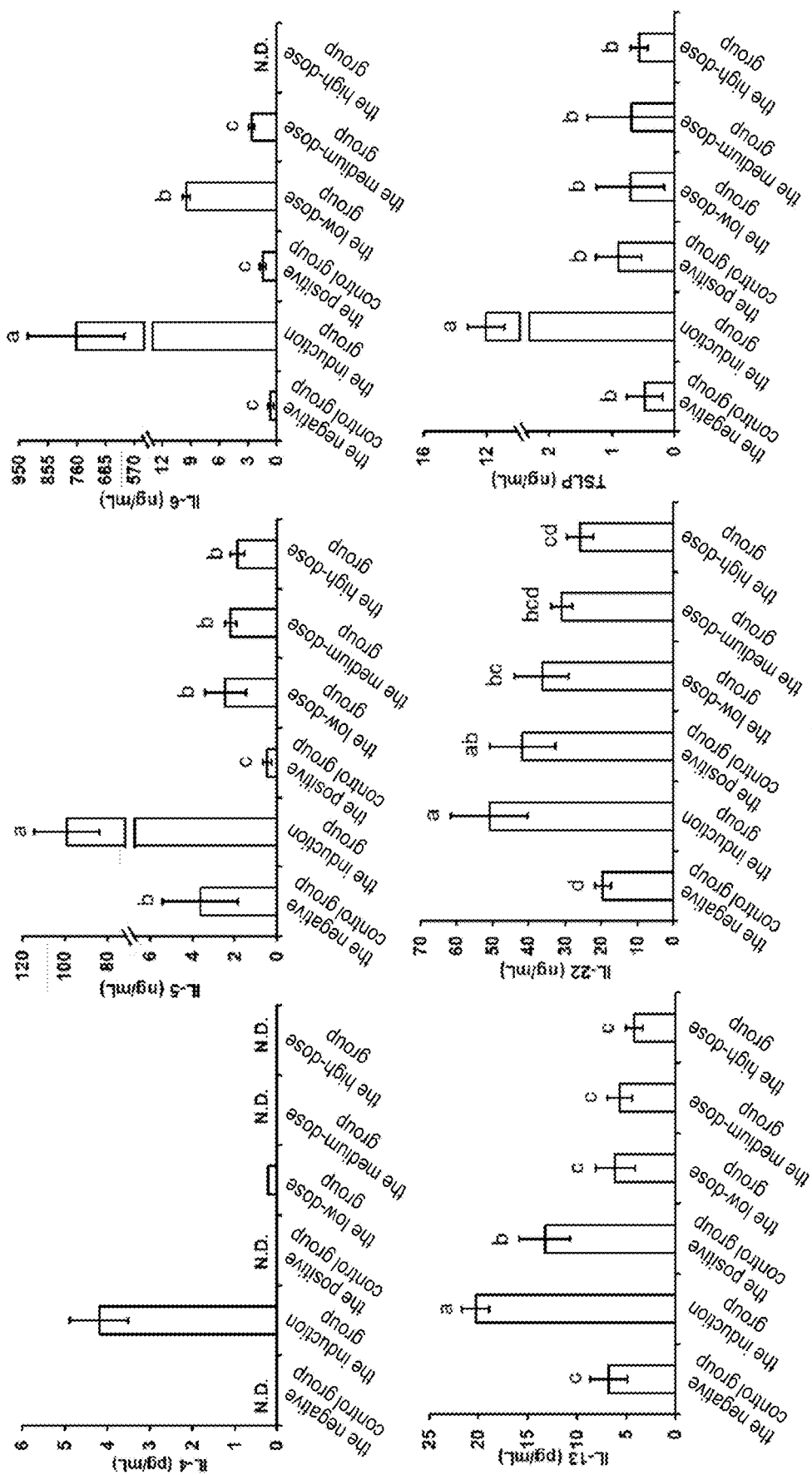
FIGS. 13A to 13B show an effect of using the oral preparation in this example on cytokines in the mouse with atopic dermatitis.
Figure 13B:
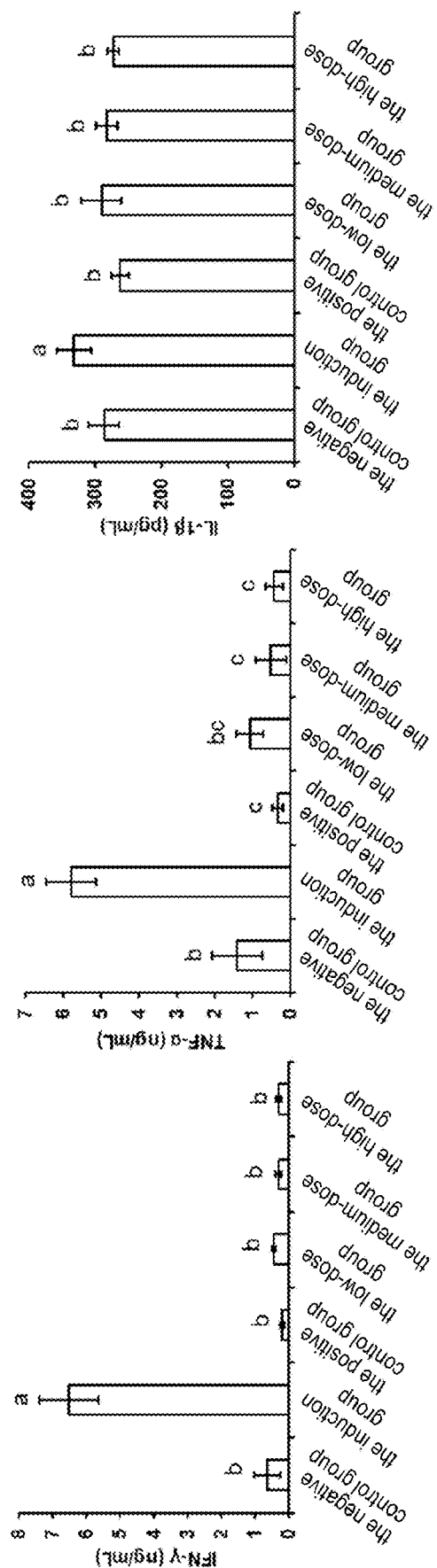

An Effect of the Oral Preparation on Cytokines in the Mouse with Atopic Dermatitis By the same or similar method as in Embodiment 8, a commercially available ProcartaPlex Mouse Simplex kit and the ELISA assay are used to measure contents of interleukin-$\beta$ (IL-1$\beta$), interleukin-4 (IL-4), interleukin-5 (IL-5), interleukin-6 (IL-6), interleukin-13 (IL-13), interleukin-22 (IL-22), thymic stromal lymphopoietin (TSLP), interferon-$\gamma\gamma$ (INF-$\gamma$), and tumor necrosis factor-$\alpha$ (TNF-$\alpha$) of the mice in each group, and results thereof are shown in FIGS. 13A and 13B. IL-4, IL-5, IL-6, IL-13, IL-22, and TSLP in FIG. 13A are cytokines related to a T helper 2 cell (Th2), and N.D. in the figure denotes NOT DETECTED. INF-$\gamma$, TNF-$\alpha$, and IL-1$\beta$ in FIG. 13B are cytokines related to the inflammation.

It may be seen form the results in FIG. 13A that compared with the negative control group where DNCB and the oral preparation are not administered, the induction group where DNCB is administered but no oral preparation is administered has significantly more contents of IL-4, IL-5, IL-6, IL-13, IL-22, and TSLP. Compared with the induction group where DNCB is administered but no oral preparation is administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the contents of IL-4, IL-5, IL-6, IL-13, IL-22, and TSLP. Compared with the induction group where DNCB is administered but no oral preparation is administered, the positive control group where DNCB and dexamethasone are administered may also significantly reduce the contents of IL-4, IL-5, IL-6, IL-13, and TSLP, but may not significantly reduce the content of IL-22.

In addition, compared with the positive control group where DNCB and dexamethasone are administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may more significantly reduce the content of IL-13. Compared with the positive control group where DNCB and dexamethasone are administered, the high-dose group where DNCB and the oral preparation containing the carbohydrate composition of 800 mg/kg are administered may more significantly reduce the content of IL-22. In all groups where DNCB and the oral preparation are administered, as the concentration of the carbohydrate composition in the oral preparation increases, the effect of inhibiting IL-6 is more obvious. Therefore, it may indicate that the oral preparation containing the carbohydrate composition may reduce the content of cytokines, that is, IL-4, IL-5, IL-6, IL-13, IL-22 and TSLP, related to the Th2, thereby improving or treating atopic dermatitis.

It may be seen form the results in FIG. 13B that compared with the negative control group where DNCB and the oral preparation are not administered, the induction group where DNCB is administered but no oral preparation is administered has significantly more contents of INF-γ, TNF-α, and IL-1β. Compared with the induction group where DNCB is administered but no oral preparation, the positive control group where DNCB and dexamethasone are administered, the low-dose group where DNCB and the oral preparation containing the carbohydrate composition of 200 mg/kg are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the contents of INF-γ, TNF-α, and IL-1β. Therefore, it may indicate that the oral preparation containing the carbohydrate composition may reduce the contents of cytokines, that is, INF-γ, TNF-α, and IL-1β, related to the inflammation, thereby improving or treating atopic dermatitis. In addition, it may also indicate that the oral preparation containing the carbohydrate composition has the effect of regulating allergic reactions in the generalized systemic circulation.

Embodiment 14

Figure 14:
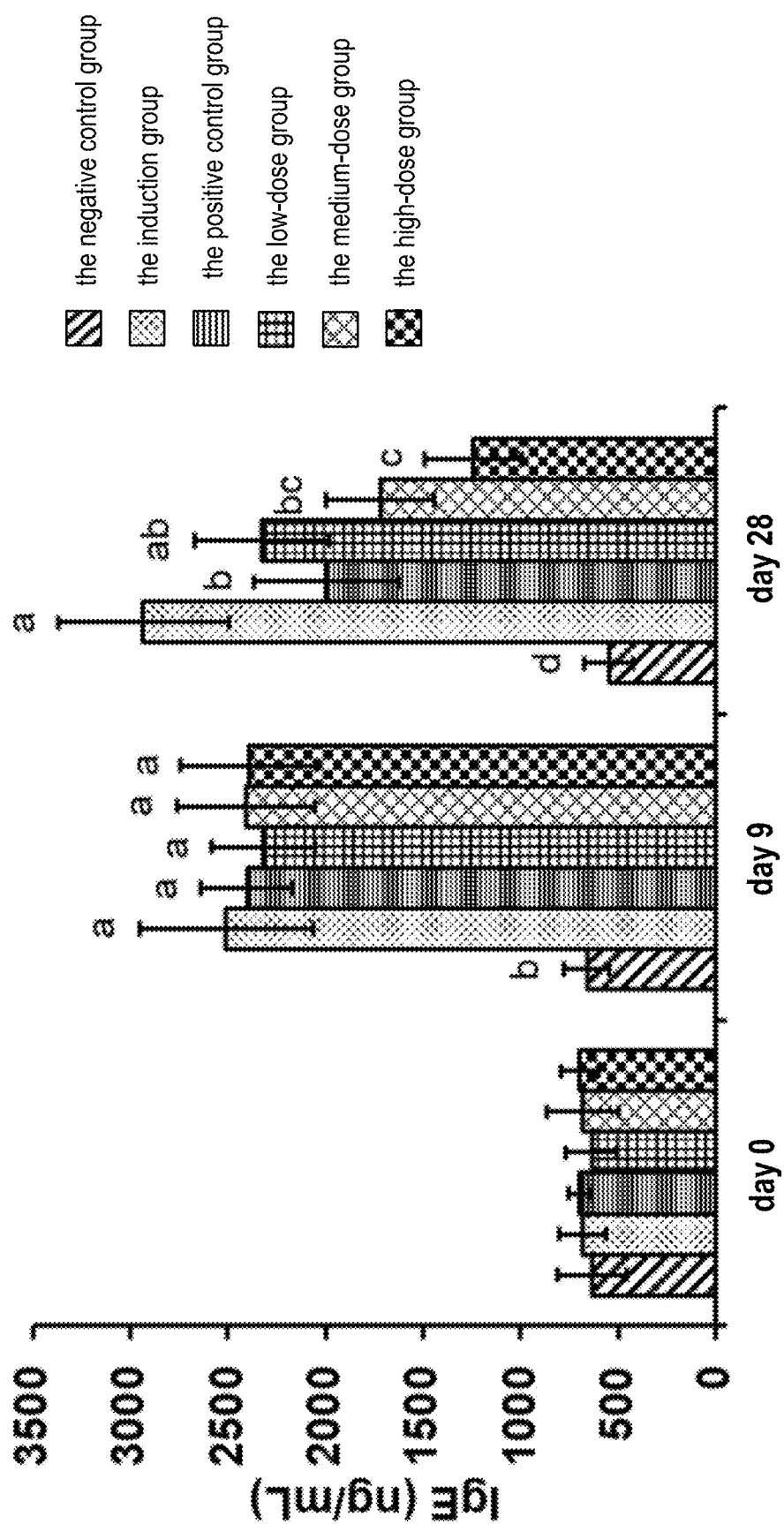
FIG. 14 shows an effect of using the oral preparation in this embodiment on the IgE in the mouse with atopic dermatitis.

An Effect of Using the Oral Preparation on the IgE in the Mouse With Atopic Dermatitis The content of IgE in the mice in each group is measured by the same or similar method as in Embodiment 8, and a result thereof is shown in FIG. 14.

It may be seen form the result on day 9 in FIG. 14 that compared with the negative control group where DNCB is not administered, the induction group where DNCB is administered, the positive control group where DNCB is administered, the low-dose group where DNCB is administered, the medium-dose group where DNCB is administered, and the high-dose group where DNCB is administered may significantly increase the content of IgE due to the induction of DNCB.

It may be seen form the result on day 28 in FIG. 14 that compared with the negative control group where DNCB and the oral preparation are not administered, the induction group where DNCB is administered but no oral preparation is administered may significantly has higher content of IgE. Compared with the induction group where DNCB is administered but no oral preparation is administered, the positive control group where DNCB and dexamethasone are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may significantly reduce the content of IgE. Compared with the positive control group where DNCB and dexamethasone are administered, the medium-dose group where DNCB and the oral preparation containing the carbohydrate composition of 400 mg/kg are administered, and the high-dose group where DNCB and the oral preparation containing the carbohydrate composition of 800 mg/kg are administered may more significantly reduce the content of IgE. Therefore, it may indicate that the oral preparation containing the carbohydrate composition may reduce the content of IgE, thereby improving or treating atopic dermatitis. In addition, it may also indicate that the oral preparation containing the carbohydrate composition has the effect of regulating the allergic reactions in the generalized systemic circulation.

Embodiments 15 to 18

Using Both the Topical Preparation and the Oral Preparation to Treat the Mouse with Atopic Dermatitis First, referring to FIG. 3, the mice with atopic dermatitis are prepared by the same or similar method as in Embodiments 4 to 8, and blood-sampling and sacrifice are performed at the same time point. However, a difference between Embodiments 15 to 18 and Embodiments 4 to 8 is that on days 14 to 28, the topical preparation is applied; gavage is performed with the oral preparation every day, or both the topical preparation is applied, and gavage is performed with the oral preparation according to the groups every day. On days 9 and 28, blood-sampling is performed to monitor the content of IgE in the serum. In addition, in this embodiment, as shown in FIGS. 15, 16, 17A to 17B, and 18, the mice are divided into 5 groups, which are a negative control group, an induction group, a topical administration group, an oral administration group, and a topical administration and oral administration group. The negative control group is the group where DNCB and the topical preparation or the oral preparation are not administered. The induction group is the group where DNCB is administered but no topical preparation or oral preparation is administered. The topical administration group is the group where DNCB and the topical preparation containing the carbohydrate composition of 70 mg/mL are administered. The oral administration group is the group where DNCB and the oral preparation containing the carbohydrate composition of 800 mg/kg are administered. The topical administration and oral administration group is the group where DNCB, the topical preparation containing the carbohydrate composition of 35 mg/mL, and the oral preparation containing the carbohydrate composition of 400 mg/kg are administered. In other words, the topical administration and oral administration group is the half-dose topical preparation (i.e., the topical preparation containing the carbohydrate composition of 35 mg/mL) in the topical administration group together with the half-dose oral preparation (i.e., the oral preparation containing the carbohydrate composition of 400 mg/kg are administered) in the oral preparation group to treat the mice with atopic dermatitis, in the hope that drug abuse in clinical applications may be reduced to achieve effective resource allocation. In addition, the topical administration and oral administration group may also provide two methods for treatment at the same time: regulating the allergic reactions in the generalized systemic circulation, and treating the lesions.

Embodiment 15

Figure 15:
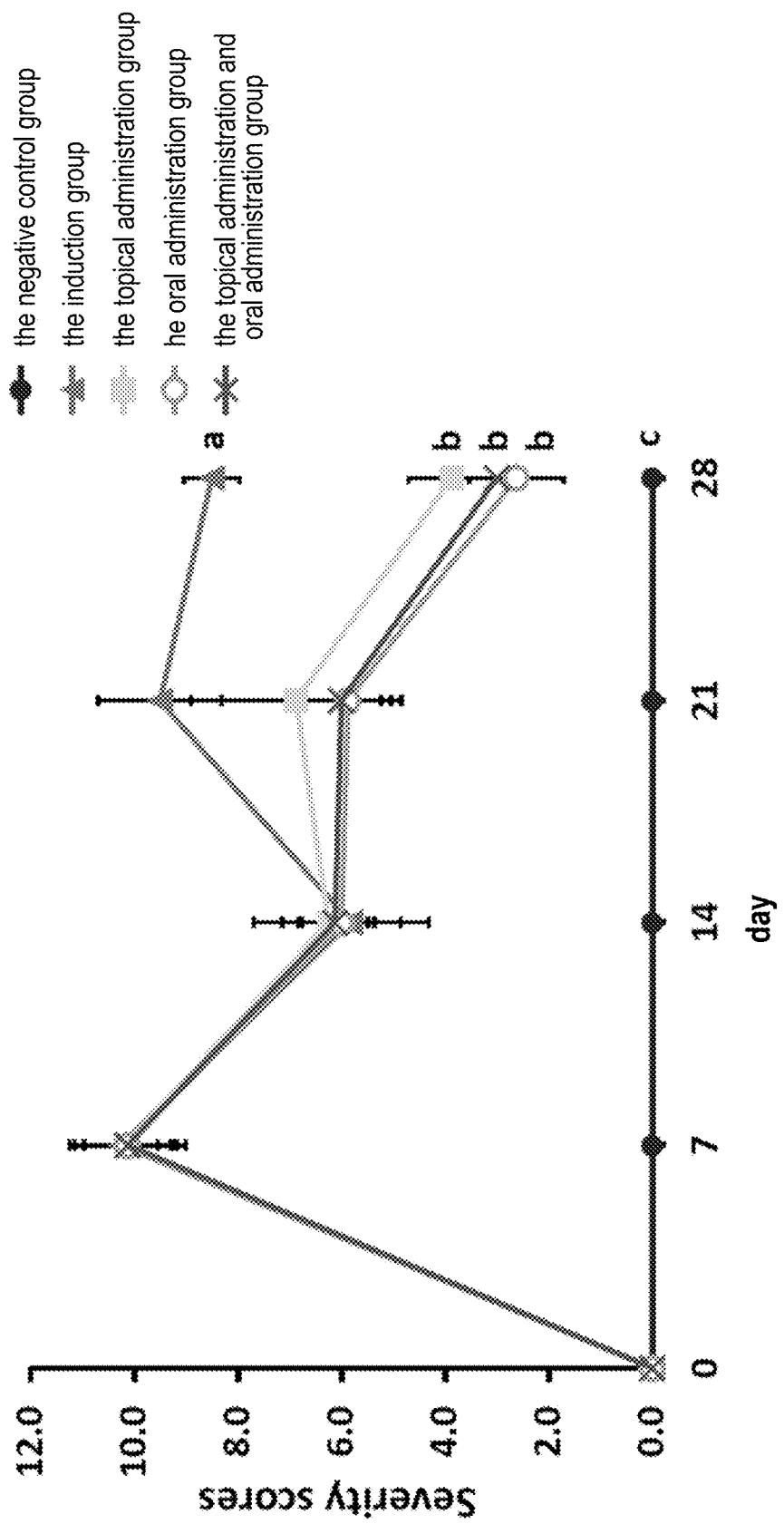
FIG. 15 shows an effect of using both the topical preparation and the oral preparation in this embodiment on the dermatitis score of the mouse with atopic dermatitis.

An Effect of Using Both the Topical Preparation and the Oral Preparation on the Dermatitis Score of the Mouse with Atopic Dermatitis The severity of atopic dermatitis and the condition of skin recovery of the mice in each group are determined on days 7, 14, 21, and 28 by the same or similar method as in Embodiment 4, and a result thereof is shown in FIG. 15.

It may be seen form the result in FIG. 15 that compared with the negative control group where DNCB and the topical preparation or the oral preparation are not administered, the induction group where DNCB is administered but no topical preparation or oral preparation is administered has significantly higher scores and more severe symptoms of skin allergies and skin inflammation. Compared with the induction group where DNCB is administered but no topical preparation or oral preparation is administered, the topical administration group where DNCB and the topical preparation containing the carbohydrate composition of 70 mg/mL are administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly reduce the scores and alleviate the symptoms of skin allergies and skin inflammation. Therefore, it may indicate that using both the half-dose topical preparation and the half-dose oral preparation may also inhibit the symptoms of skin allergies and skin inflammation, thereby repairing the skin and improving or treating atopic dermatitis. In addition, the effect of the topical administration and oral administration group in inhibiting the symptoms of skin allergies and skin inflammation is similar to the effect of the topical administration group or the oral administration group in inhibiting the symptoms of skin allergies and skin inflammation. Therefore, it may indicate that using both the half-dose topical preparation and the half-dose oral preparation may have additive effects in inhibiting the symptoms of skin allergies and skin inflammation.

Embodiment 16

Figure 16:
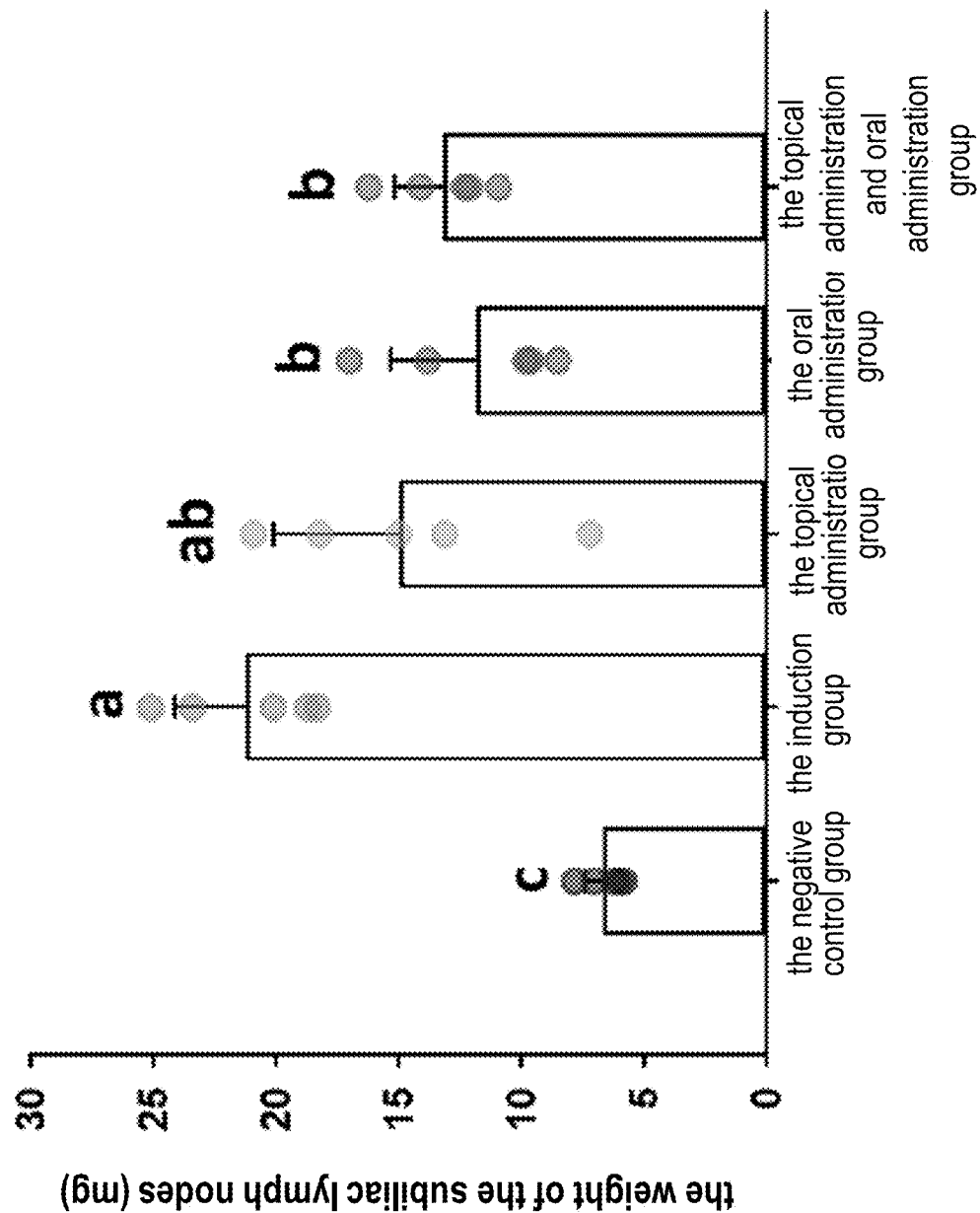
FIG. 16 shows an effect of using both the topical preparation and the oral preparation in this embodiment on the subiliac lymph nodes of the mouse with atopic dermatitis.

An Effect of Using Both the Topical Preparation and the Oral Preparation on the Subiliac Lymph Nodes of the Mouse with Atopic Dermatitis The weight of the subiliac lymph nodes of the mice in each group is measured by the same or similar method as in Embodiment 5, and a result thereof is shown in FIG. 16.

It may be seen from the result in FIG. 16 that compared with the negative control group where DNCB and the topical preparation or the oral preparation are not administered, the induction group where DNCB is administered but no topical preparation or oral preparation is administered has significantly heavier subiliac lymph nodes. Compared with the induction group where DNCB is administered but no topical preparation or oral preparation is administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly reduce the weight of the subiliac lymph nodes. Therefore, it may indicate that using both the half-dose topical preparation and the half-dose oral preparation may reduce the inflammation and swelling of the subiliac lymph nodes, thereby improving or treating atopic dermatitis. In addition, the effect of the topical administration and oral administration group in reducing the inflammation and swelling of the subiliac lymph nodes is similar to the effect of the topical administration group or the oral administration group in reducing the inflammation and swelling of the subiliac lymph nodes. Therefore, it may indicate that using both the half-dose topical preparation and the half-dose oral preparation may have the additive effects in reducing the inflammation and swelling of the subiliac lymph nodes.

Embodiment 17

Figure 17A:
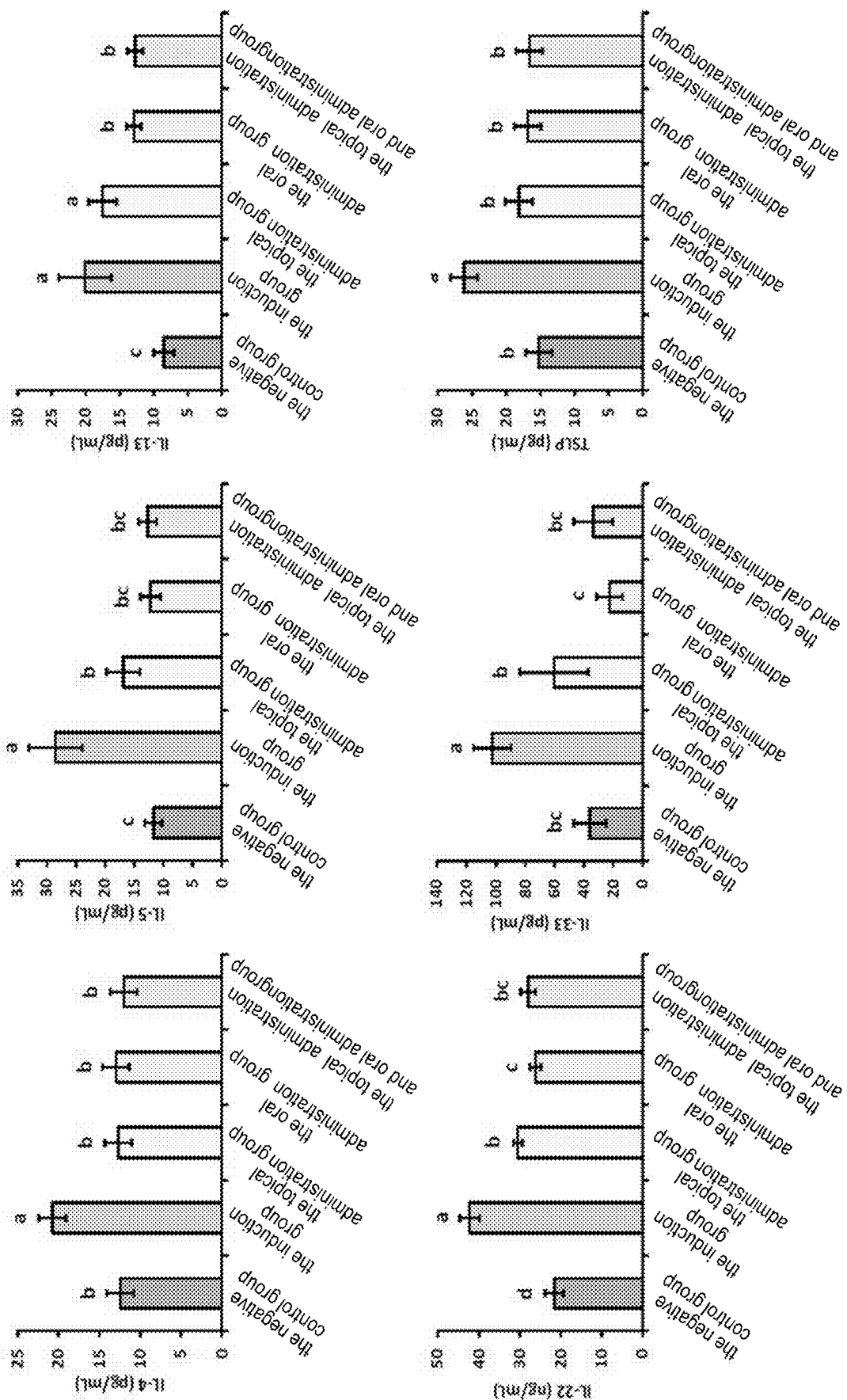
FIGS. 17A to 17B show an effect of using both the topical preparation and the oral preparation in this example on the cytokines in the mouse with atopic dermatitis.
Figure 17B:
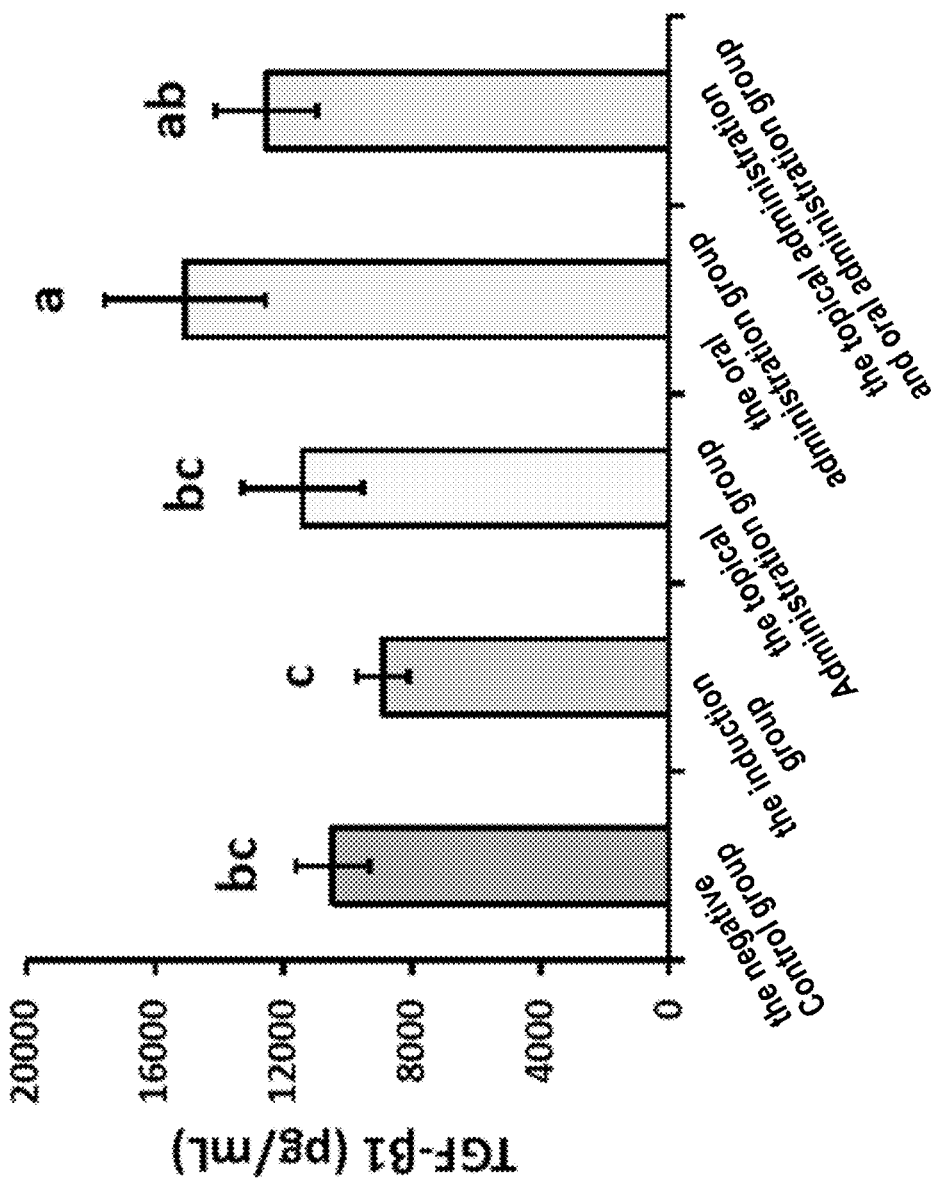

An Effect of Using Both the Topical Preparation and the Oral Preparation on the Cytokines in the Mouse with Atopic Dermatitis By the same or similar method as in Embodiment 8, the commercially available ProcartaPlex Mouse Simplex kit and the ELISA assay are used to measure the contents of interleukin-4 (IL-4), interleukin-5 (IL-5), interleukin-13 (IL-13), interleukin-22 (IL-22), interleukin-33 (IL-33), TSLP, and transforming growth factor-β1 (TGF-β1), and results thereof are shown in FIGS. 17A and 17B. IL-4, IL-5, IL-13, IL-22, IL-33, and TSLP in FIG. 17A are the cytokines related to the Th2.

It may be seen form the results in FIG. 17A that compared with the negative control group where DNCB and the topical preparation or the oral preparation are not administered, the induction group where DNCB is administered but no topical preparation or oral preparation is administered has significantly more contents of IL-4, IL-5, IL-13, IL-22, IL-33, and TSLP. Compared with the induction group where DNCB is administered but no topical preparation or oral preparation is administered, the topical administration group where DNCB and the topical preparation containing the carbohydrate composition of 70 mg/mL are administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly reduce the contents of IL-4, IL-5, IL-22, IL-33, and TSLP. Compared with the induction group where DNCB is administered but no topical preparation or oral preparation is administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly reduce the content of IL-13. Therefore, it may indicate that using both the half-dose topical preparation and the half-dose oral preparation may reduce the content of cytokines, that is, IL-4, IL-5, IL-13, IL-22, IL-33, and TSLP, related to the Th2, thereby improving or treating atopic dermatitis. In addition, the effect of the topical administration and oral administration group in reducing the content of cytokines related to the Th2 is similar to the effect of the topical administration group or the oral administration group in reducing the content of cytokines related to the Th2. Therefore, it may indicate that using both the half-dose topical preparation and the half-dose oral preparation may have the additive effects in reducing the content of cytokines related to the Th2.

It may be seen from the result in 17B that compared with the induction group where DNCB is administered but no topical preparation or oral preparation is administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly increase the content of TGF-β1. Therefore, it may indicate that using the oral preparation individually, or using both the half-dose topical preparation and the half-dose oral preparation may increase the content of TGF-β1, thereby improving or treating atopic dermatitis. In addition, the effect of the topical administration and oral administration group in increasing the content of TGF-β1 is similar to the effect of the topical administration group or the oral administration group in increasing the content of TGF-β1. Therefore, it may indicate that using both the half-dose topical preparation and the half-dose oral preparation may have the additive effects in increasing the content of TGF-β1.

Embodiment 18

Figure 18:
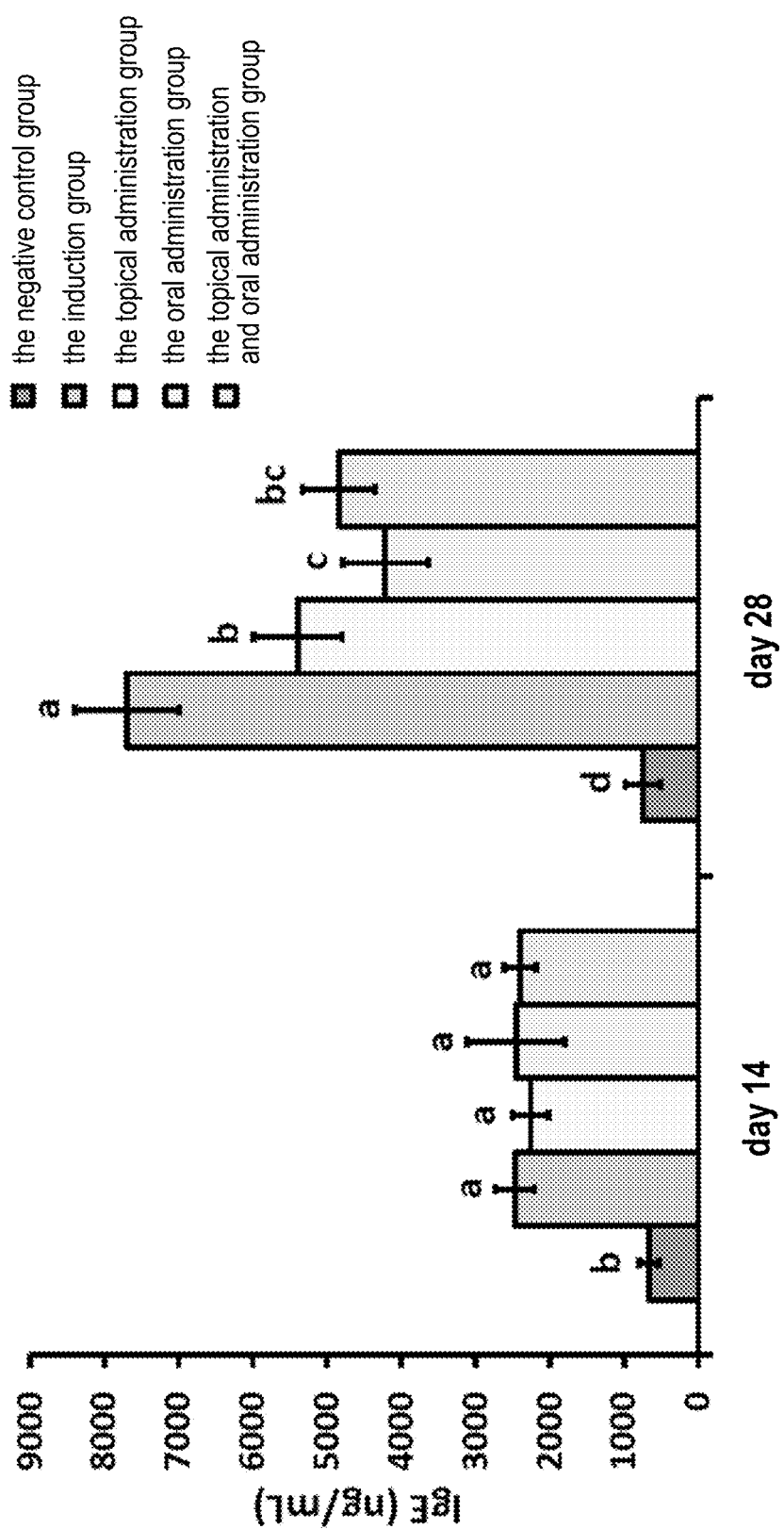
FIG. 18 shows an effect of using both the topical preparation and the oral preparation in this embodiment on the IgE in the mouse with atopic dermatitis.

An Effect of Using Both the Topical Preparation and the Oral Preparation on the IgE in the Mouse with Atopic Dermatitis The content of IgE in the mice in each group is measured by the same or similar method as in Embodiment 8, and a result thereof is shown in FIG. 18.

It may be seen form the result on day 14 in FIG. 18 that compared with the negative control group where DNCB is not administered, the induction group where DNCB is administered, the topical administration where DNCB is administered, the oral administration group where DNCB is administered, and the topical administration and oral administration group where DNCB is administered may significantly increase the content of IgE due to the induction of DNCB.

It may be seen form the result on day 28 in FIG. 18 that compared with the negative control group where DNCB and the topical preparation or the oral preparation are not administered, the induction group where DNCB is administered but no topical preparation or oral preparation is administered may significantly has higher content of IgE. Compared with the induction group where DNCB is administered but no topical preparation or oral preparation is administered, the topical administration group where DNCB and the topical preparation containing the carbohydrate composition of 70 mg/mL are administered, the oral administration group where DNCB and the oral preparation containing the carbohydrate composition of 800 mg/kg are administered, and the topical administration and oral administration group (i.e., the group including DNCB, the topical preparation containing the carbohydrate composition of 35 mg/mL, and the oral preparation containing the carbohydrate composition of 400 mg/kg) may significantly reduce the contents of IgE. Therefore, it may indicate that using both the half-dose topical preparation and the half-dose oral preparation may reduce the contents of IgE, thereby improving or treating atopic dermatitis. In addition, the effect of the topical administration and oral administration group in reducing the contents of IgE is similar to the effect of the topical administration group or the oral administration group in reducing the contents of IgE. Therefore, it may indicate that using both the half-dose topical preparation and the half-dose oral preparation may have the additive effects in reducing the contents of IgE.

Based on the above, in the carbohydrate composition and the pharmaceutical ingredient in the embodiments of the disclosure, the carbohydrate composition may include fucose of 45.5% to 76% by weight, glucuronic acid of 11% to 19% by weight, galactose of 4.5% to 14.5% by weight, and arabinose of 5.5% to 18% by weight. Therefore, the carbohydrate composition and the pharmaceutical ingredient containing the carbohydrate composition may inhibit the production of nitric oxide due to LPS stimulation, inhibit the degranulation of the mast cells, inhibit IL-4 and histamine produced by the mast cells due to the degranulation, inhibit the symptoms of skin allergies and skin inflammation, reduce the inflammation and swelling of the subiliac lymph nodes, slow down thickening of the epidermis, reduce the infiltration of eosinophilic granules in the dermis, reduce the contents of IL-4, IL-5, IL-6, IL-13, IL-22, IL-33, and TSLP, reduce the contents of INF-γ, TNF-α, and IL-1β, increase the content of TGF-β1, and reduce the content of IgE, thereby having the effects of nourishing the skin, inhibiting skin allergies, inhibiting skin inflammation, or improving atopic dermatitis, and having no side effects.

Although the disclosure has been described with reference to the above embodiments, they are not intended to limit the disclosure. It will be apparent to one of ordinary skill in the art that modifications to the described embodiments may be made without departing from the spirit and the scope of the disclosure. Accordingly, the scope of the disclosure will be defined by the attached claims and their equivalents and not by the above detailed descriptions.

What is claimed is:

1. A method of using a pharmaceutical ingredient, comprising:
preparing the pharmaceutical ingredient comprising an effective amount of a carbohydrate and an additive for oral and/or topical administration; and
administering the pharmaceutical ingredient for a period consisting of more than 28 days to inhibit skin allergies, skin inflammation and atopic dermatitis of a patient by reducing IL-6, IL-13, IL-22, IL-33, TSLP, IFN-γ, TNF-α and IL-1β, and increasing TGF-β1 in the serum,
wherein the carbohydrate is derived from a cladosiphon okamuranus extract, and
based on a total weight of the carbohydrate, a content of the fucose is 45.5% to 76% by weight, a content of the glucuronic acid is 11% to 19% by weight, a content of the galactose is 4.5% to 14.5% by weight, a content of the arabinose is 5.5% to 18% by weight, and a content of other components of the carbohydrates is up to 3.5% by weight,
wherein the additive comprises an excipient, a solvent, a diluent, a pigment, a flavoring agent, a thickener, or a combination of distinct additives thereof.

2. A method for nourishing skin, comprising:
preparing health food or a care product, wherein the health food or the care product comprises an effective amount of a carbohydrate and an additive for oral and/or topical administration; and
administering the health food or the care product for a period consisting of more than 28 days to nourish skin of a person,
wherein the carbohydrate is derived from a cladosiphon okamuranus extract, and
based on a total weight of the carbohydrate, a content of the fucose is 45.5% to 76% by weight, a content of the glucuronic acid is 11% to 19% by weight, a content of the galactose is 4.5% to 14.5% by weight, a content of the arabinose is 5.5% to 18% by weight, and a content of other components of the carbohydrates is up to 3.5% by weight,
wherein the additive comprises an excipient, a solvent, a diluent, a pigment, a flavoring agent, a thickener, or a combination of distinct additives thereof.

3. The method according to claim 1, wherein based on the total weight of the carbohydrate, the content of the fucose is 49.5% to 72.5% by weight, the content of the glucuronic acid is 11% to 17.5% by weight, the content of the galactose is 6% to 14% by weight, and the content of the arabinose is 8.5% to 16% by weight.

4. The method according to claim 1, wherein based on the total weight of the carbohydrate, the content of the fucose is 52% to 69% by weight, the content of the glucuronic acid is 11.5% to 17% by weight, the content of the galactose is 6.5% to 13.5% by weight, and the content of the arabinose is 9% to 15.5% by weight.

5. The method according to claim 1, wherein the pharmaceutical ingredient is an oral preparation.

6. The method according to claim 5, wherein a dose range of the carbohydrate in the oral preparation ranges from 50 mg/kg to 800 mg/kg.

7. The method according to claim 1, wherein the pharmaceutical ingredient is a topical preparation.

8. The method according to claim 7, wherein a dose range of the carbohydrate in the topical preparation ranges from 35 mg/mL to 70 mg/mL.

9. The method according to claim 1, wherein the carbohydrate is a topical preparation and an oral preparation.

10. The method according to claim 9, wherein a dose range of the carbohydrate in the topical preparation ranges from 35 mg/mL to 70 mg/mL, and a dose range of the carbohydrate in the oral preparation ranges from 50 mg/kg to 800 mg/kg.

11. The method according to claim 1, wherein the pharmaceutical ingredient inhibits skin allergies, skin inflammation and atopic dermatitis of the patient by inhibiting nitric oxide, degranulation of mast cells, histamine, inflammation and swelling of subiliac lymph nodes, thickening of epidermis, and infiltration of eosinophilic granules.

* * * * *